United States Patent [19]
Effland et al.

[11] Patent Number: 5,110,815
[45] Date of Patent: May 5, 1992

[54] 5-AMINO-5,6,7,8-TETRAHYDROQUINOLINES AND RELATED COMPOUNDS AND PHARMACEUTICAL USE

[75] Inventors: Richard C. Effland, Bridgewater, N.J.; David Fink, Doylestown, Pa.

[73] Assignee: Hoechst-Roussel Pharmaceuticals Inc., Somerville, N.J.

[21] Appl. No.: 620,811

[22] Filed: Dec. 3, 1990

[51] Int. Cl.$^5$ .................. A61K 31/47; C07D 215/227
[52] U.S. Cl. ........................ 514/228.2; 514/235.2; 514/249; 514/312; 544/58.6; 544/128; 544/363; 546/157; 546/183
[58] Field of Search ...................... 544/58.6, 128, 363; 546/157, 183; 514/228.2, 235.2, 249, 312

[56] References Cited
PUBLICATIONS
R. Albrecht and E. Schroder, Arch. Pharmaz., 308; 588 (1975) and English Translation.
L. Mosti, et al., Journal of Heterocyclic Chemistry, 22, 1503 (1985).
Y. C. Martin, et al., Journal of Medicinal Chemistry, 16, 147 (1973).

Primary Examiner—Richard L. Raymond
Attorney, Agent, or Firm—Raymond R. Wittekind

[57] ABSTRACT

Novel 5-amino-5,6,7,8-tetrahydroquinolines and related compounds, intermediates and processes for the preparation thereof, and methods for relieving memory dysfunction utilizing compounds or compositions thereof are disclosed.

46 Claims, No Drawings

5-AMINO-5,6,7,8-TETRAHYDROQUINOLINES AND RELATED COMPOUNDS AND PHARMACEUTICAL USE

The present invention relates to tetrahydroquinolines and related compounds. More particularly, the present invention relates to 5-amino-5,6,7,8-tetrahydroquinolines of the formula

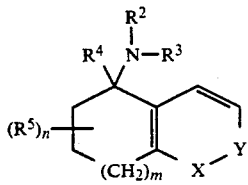

wherein X-Y is a group of the formula

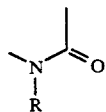

wherein R is hydrogen, alkyl, alkenyl, alkynyl, or arylalkyl, or a group of the formula

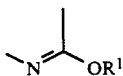

wherein $R^1$ is hydrogen, alkyl or arylalkyl; $R^2$ and $R^3$ are independently hydrogen, alkyl, arylalkyl, diarylalkyl, cycloalkenylalkyl, alkoxy, arylalkoxy, or alkanoyl; $R^2$ and $R^3$ taken together with the nitrogen atom to which they are attached form a group of the formula

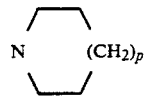

wherein p is 0 or 1, a group of the formula

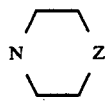

wherein Z is O, S, or a group of the formula $NR^6$ wherein $R^6$ is hydrogen, alkyl, or arylalkyl; $R^4$ is hydrogen, alkyl or arylalkyl; $R^5$ is hydrogen, alkyl or arylalkyl; and m is 0, 1, or 2, and n is 1 or 2; or geometrical and optical isomers thereof, or a pharmacuetically acceptable salt thereof, which are useful for relieving memory dysfunction, for example, memory dysfunction such as that associated with reduced cholinergic function in Alzheimer's disease alone or in combination with adjuvants.

Subgeneric to the 5-amino-5,6,7,8-tetrahydroquinolines of the present invention are compounds wherein:
a. X-Y is a group of the formula

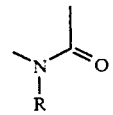

and m is 1; and
b. X-Y is a group of the formula

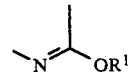

and m is 1.

The present invention also relates to 5-hydroxy-5,6,7,8-tetrahydroisoquinolines of the formula

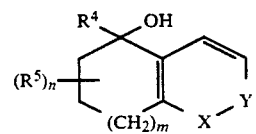

wherein X-Y is a group of the formula

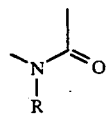

wherein R is hydrogen, alkyl, alkenyl, alkynyl, or arylalkyl, or a group of the formula

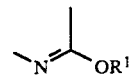

wherein $R^1$ is alkyl or arylalkyl; $R^4$ is hydrogen, alkyl, or arylalkyl; $R^5$ is hydrogen, alkyl, or arylalkyl; and m is 0, 1, or 2; and n is 1 or 2; or the geometric or optical isomers thereof,, which are useful as intermediates for the preparation of the present 5-amino-5,6,7,8-tetrahydroquinolines.

As used throughout the specification and appended claims, the term "alkyl" shall mean a straight or branched chain hydrocarbon group containing no unsaturation and having from 1 to 8 carbon atoms. Examples of alkyl groups are methyl, ethyl, propyl, isopropyl, neopentyl, tert-pentyl, hexyl, pentyl, and octyl, and the like. The term "alkenyl" shall mean a straight or branched chain hydrocarbon group containing one carbon to carbon double bond and having 3 to 8 carbon atoms. Examples of alkenyl groups are propenyl, butenyl, pentenyl, hexenyl, heptenyl, octenyl, and the like. The term "alkynyl" refers to a straight or branched chain hydrocarbon radical containing unsaturation in the form of a single carbon to carbon triple bond and having from 3 to 7 carbon atoms such as 2-propynyl, 2-butynyl, 1-methyl-2-butynyl, 4-methyl-2-pentynyl, 4,4-dimethyl-2-butynyl and the like. The term "cycloalkenyl" refers to a hydrocarbon group having one carbocyclic ring of 4 to 6 carbon atoms and one carbon-to-carbon double bond. Examples of cycloalkenyl groups are cyclobutenyl, cyclopentenyl, and cyclohexenyl. The term "aryl" shall mean phenyl or phenyl substituted by one or more chloro, bromo, fluoro, methoxy, alkyl of from 1 to 8 carbon atoms, nitro, hydroxy, or trifluoromethyl groups. The term "aralkyl" refers to a radical formed by attachment of an alkyl function to an aryl moiety. The term "alkanol" refers to a compound formed by a combination of an alkyl group and a hydroxy radical. Examples of alkanols are methanol, ethanol, 1- and 2-propanol, 1,2-dimethylethanol, hexanol, octanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid and the like. The term "halogen" refers to a member of the family consisting of fluorine, chlorine, bromine or iodine. The term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl and the like. The term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy, octoxy. The term "lower" as applied to any of the aforementioned groups shall mean a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optica resolution techniques, involving, for example, the separation of diastereomeric salts of those instant compounds characterized by the presence of a basic amino group and an optically active acid, or by synthesis from optically active precursors.

The present invention comprehends all optical isomers and racemic forms thereof of the compounds disclosed and claimed herein and the formulas of the compounds shown herein are intended to encompass all possible optical isomers of the compounds so depicted.

The novel 5-amino-5,6,7,8-tetrahydroquinolines and related compounds of the present invention are synthesized by the processes illustrated in Reaction Schemes A and B. The following discussion focuses on the tetrahydroquinoline series. The processes shown in the Reaction Schemes may be applied to the synthesis of the related compounds.

To gain entry into the primary amino-5,6,7,8-tetrahydroquinoline system 1a/1b, i.e., to prepare a tautomeric 2-hydroxy-5,6,7,8-tetrahydroquinoline 1a/5,6,7,8-tetrahydro-2(1H)-quinolinone 1b, characterized by the presence of a primary amino group (NH₂), a 5-oxo-5,6,7,8-tetrahydro-2(1H)-quinolinone 2 (shown as one tautomer), the preparation of which is described in L. Mosti, et al., Journal of Heterocyclic Chemistry, 22, 1503 (1985), is O-alkylated to a 2-alkoxy-(or -arylalkoxy)-5-oxo-5,6,7,8-tetrahydroquinoline 3, which is converted to a 2-alkoxy -(or -aryloxy)-5-hydroxy-5,6,7,8-tetrahydroquinoline 4 and aminated to a 5-alkanoylamino-2-alkoxy-(or arylalkoxy)-5,6,7,8-tetrahyroquinoline 5. In turn, a 5-alkanoylamino-2-alkoxy-(or arylalkoxy)-5,6,7,8-tetrahydroquinoline 5 is cleaved to a 5-alkanoylamino-2-hydroxy-5,6,7,8-tetrahydroquinoline 6a/5-alkanoylamino-5,6,7,8-tetrahydro-2(1H)-quinolinone 6b and hydrolyzed to a primary aminoquinoline 1a/1b.

The O-alkylation is conveniently performed by treating a 2(1H)-quinolinone 2 with a halide of formula 11

$$R^1Hal \quad (11)$$

wherein $R^1$ is alkyl or arylalkyl and Hal is halogen in an aromatic solvent such as, for example, benzene, toluene, xylene, mesitylene, and the like, in the presence of a base such as sodium carbonate, potassium carbonate, or silver carbonate. Toluene and silver carbonate are preferred. The alkylation proceeds readily at about ambient temperature (about 25° C.). Reduced temperatures (about 0° to about 25° C.) and elevated temperatures (about 25° to about 50° C.) may be employed, however.

The conversion of a 5-oxoquinoline 3 to a 5-hydroxyquinoline 4 wherein $R^4$ is alkyl or arylalkyl is effected by the Grignard technique. Thus, treatment of a 5-oxoquinoline 3 with a Grignard reagent of formula 12

$$R^4MgHal \quad (12)$$

wherein $R^4$ is alkyl or arylalkyl and Hal is as above in an aromatic solvent (e.g., benzene, toluene, xylene, or mesitylene) or an ethereal solvent (e.g., diethyl ether, 2-methoxyethyl ether, tetrahydrofuran, and dioxan) at a reaction temperature of from about 0° to about 50° C. provides a 5-hydroxyquinoline 4 wherein $R^4$ is as above. An aromatic solvent is preferred; toluene is most preferred. The preferred reaction temperature is about 25° C. A 5-hydroxyquinoline 4 wherein $R^4$ is hydrogen may be prepared by reduction of a 5-oxoquinoline 4 with, for example, an alkali metal borohydride such as sodium borohydride or potassium borohydride in an alkanol such as ethanol or 2-propanol under conventional conditions.

The amination of a 5-hydroxy-5,6,7,8-tetrahydroquinoline 4 to a 5-alkanoylamino-5,6,7,8-tetrahydroquinoline 5 is accomplished by treating a carbinol 4 with a nitrile of formula 13

$$R^7CN \quad (13)$$

wherein $R^7$ is alkyl in the presence of a strong acid. Included among strong acids are mineral acids, e.g., hydrochloride acid, hydrobromic acid, and sulfuric acid, and organic acids, e.g., sulfonic acids such as benzenesulfonic acid and para-toluenesulfonic acid, and carboxylic acids such as trifluoroacetic acid. Mineral acids are preferred; sulfuric acid is most preferred. The amination is generally performed in excess reactant 13, the nitrile acting both as the aminating agent and solvent. The reaction temperature is not narrowly critical and proceeds at a convenient rate at about 25° C. (ambient temperature). Reduced temperatures within the range from about 0° to about 25° C. and elevated temperatures within the range from about 25° to about 50° C. may be employed, depending upon the specific reactants.

The cleavage of a 2-arylalkoxy-5,6,7,8-tetrahydroquinoline 5 wherein $R^1$ is phenylmethyl or substituted phenylmethyl to a 2-hydroxy-5,6,7,8-tetrahydroquinoline 6a/5,6,7,8-tetrahydro-2(1H)-quinolinone 6b is carried out at about 25° C., under hydrogenolysis conditions in an alkanol such as methanol, ethanol, or 1- or 2-propanol, ethanol being preferred, in the presence of a noble metal catalyst, supported or unsupported, such as palladium-on-carbon, platinum, rhodium-on-alumina, or ruthenium, 10% palladium-on-carbon, being preferred, under hydrogen pressure within the range of about 25 to about 85 pounds per square inch (psi), about 55 psi of hydrogen being preferred. The hydrolysis of a 5-alkanoylamino-5,6,7,8-tetrahydroquinoline 6a/5-alkanoylamino-5,6,7,8-tetrahydro-2(1H)-quinolinone 6b to the ultimate primary 5-aminoquinoline 1a/5-amino-2(1H)-quinolinone 1b may be achieved by conventional basic hydrolysis (e.g., sodium hydroxide or potassium hydroxide in methanol or ethanol) or acidic hydrolysis (e.g., hydrochloric acid or sulfuric acid in ethanol or 2-propanol) methods.

Alternatively, a tautomeric primary amino-5,6,7,8-tetrahydroquinoline 1a/1b is prepared by condensing a 5,6,7,8-tetrahydroquinolinol 4 with an alkoxyamine of formula 14

$$R^8CH_2ONH_2 \quad (14)$$

wherein $R^8$ is pheny or phenyl substituted by one or more halogen, alkoxy, alkyl, or trifluoromethyl groups to yield a methoxyamino-5,6,7,8-tetrahydroquinoline 7 which is first cleaved to a 5,6,7,8-tetrahydroquinolinamine 8 and then to a tautomeric aminoquinoline 1a/1b. The condensation, an amination, is achieved by contacting a tetrahydroquinolinol 4 with a methoxyamine 14, in the presence of a strong mineral or organic acid in an aromatic solvent. Included among strong mineral acids are hydrohalic acids, for example, hydrochloric acid, hydrobromic acid, and the like, and sulfuric acid, nitric acid, and phosphoric acid. Included among strong organic acids are dihaloalkanoic acids, for example, dichloroacetic acid, trihaloalkanoic acids, for example, trifluoroacetic acid, and arylsulfonic acids, for example, phenylsulfonic acid, 4-tolylsulfonic acid, 2-naphthalenesulfonic acid, and the like. Included among aromatic solvents are benzene, toluene, xylene, and mesitylene. Trifluoroacetic acid and toluene are the preferred strong acid and aromatic solvent. The amination is generally conducted at about 25° C. Higher (from about 25° C. to the boiling point of the reaction mixture) and lower (from about 0° C. to about 25° C.) may be employed. An amination temperature of about 25° C. is preferred.

The first cleavage, i.e., the cleavage of the methoxyamino function of 7 to provide the primary amino function of 8 is accomplished in an ethereal solvent such as tetrahydrofuran, dioxane, 1,2-dimethoxyethane, 2-methoxyethyl ether, and diethyl ether by means of a borane complex, for example, borane tetrahydrofuran complex. Elevated cleavage temperatures of about 50° C. to about the reflux temperature are preferred.

The second cleavage reaction, namely, the hydrogenolyis of the benzyl ether function of 8 to afford a tautomeric aminoquinoline 1a/1b is effected by the processes described above for the cleavage of a 2-arylalkoxyquinoline 5 to a tautomer 6a/6b.

A 1-alkyl-, 1-alkenyl- or 1-arylalkyl-5-amino-5,6,7,8-tetrahydro-2(1H)-quinolinone 10 is constructed by alkylating a tautomeric 5-aminoquinoline 1a/1b with a halide of formula 15.

$$R^9Hal \quad (15)$$

wherein $R^9$ is alkyl, alkenyl, or arylalkyl and Hal is as before. The alkylation is performed by first abstracting a proton from the tautomer 1a/1b with, for example, an alkali metal hydride in an aprotic dipolar solvent, and treating the anion, so formed, with a halide 15. Suitable alkali metal hydrides include lithium hydride, sodium hydride, and potassium hydride. Suitable aprotic dipolar solvents include dimethylacetamide, dimethylformamide, dimethylsulfoxide, and hexamethylphosphoramide. An alkylation employing an alkyl, alkenyl-, or arylalkyl iodide, i.e., a halide 15 wherein Hal is iodo, and sodium hydride in dimethylformamide is preferred. The alkylation of tautomer 1a/1b to a 1-substituted derivative 10 proceeds readily at about 25° C. Elevated temperatures within the range of about 25° to about 50° C. and reduced temperatures within the range of about 5° to about 25° C. may be employed to effect the desired transformation.

To gain entry into the secondary amino-5,6,7,8-tetrahydroquinoline system 17a/17b, i.e., to prepare a tautomeric 2-hydroxy-5,6,7,8-tetrahydroquinoline 17a/5,6,7,8-tetrahydro-2(1H)-quinolinone 17b, characterized by the presence of a secondary amino group (NHR²), an arylmethoxy-5,6,7,8-tetrahydroquinolinamine 7 is alkylated to an N-alkyl-, (-or N-arylalkyl)-N-arylmethoxy-5,6,7,8-tetrahydroquinolinamine 9, which is first cleaved at the amino function to give an N-alkyl-, (or N-arylalkyl)-5,6,7,8-tetrahydroquinolinamine 16 and then at the oxygen function to yield a tautomeric 5,6,7,8-tetrahydroquinoline 17a/17b. The alkylation of an alkoxyamine 7 to an N-alkylalkoxyamine 9 is carried out by forming the amino anion with an organometallic, for example, an alkylalkali metal such as methyllithium or an arylalkali metal such as phenyllithium in an ethereal solvent such as diethyl ether, tetrahydrofuran, dioxane, 1,2-dimethoxyethane, 2-methoxyethyl ether, or combinations thereof, and treating the anion, so formed, with a halide 15. The anion formation is preferably carried out at a reduced temperature of about −78° C., while the alkylation of the anion is preferably performed at about 25° C.

The cleavages of the N-arylmethoxy group of 9 and the O-arylalkyl group of 16 are achieved by processes substantially similar to those utilized for the conversions of 7 to 8 and 5 to 6a/6b, described above.

In an alternative approach to a secondary amino-5,6,7,8-tetrahydroquinolinone 21 and a tautomeric 5,6,7,8-tetrahydroquinolinone/5,6,7,8-tetrahydroquinolinone 25a/25b, a 1-alkyl-5-oxo-5,6,7,8-tetrahydro-2(1H)-quinolinone 19, prepared according to the procedures outlined in R. Albrecht and E. Schröder, Arch. Pharmaz., 308, 588 (1975), is condensed with a primary amine of formula 22.

$$R^2R^3NH \quad (22)$$

wherein $R^2$ is alkyl or arylalkyl and $R^3$ is hydrogen to provide an intermediate imine of formula 20 wherein the bond (—) is between the C-5 carbon atom and the amino nitrogen which is reduced to a secondary 5-alkyl- or 5-arylalkylamino-5,6,7,8-tetrahydro-2(1H)-quinolinone 21. The condensation, providing an intermediate imine 20, is conducted in the presence of a strong carboxylic or sulfonic acid such as, for example, trifluoroacetic acid, or benzenesulfonic or para-toluenesulfonic acid in an aromatic solvent such as, for example, benzene or toluene, optionally with azeotropic removal of the water formed in the reaction. While the amount of strong acid used to promote the condensation is not critical, catalytic amounts are preferred. para-Toluenesulfonic acid and toluene are the preferred strong acid and aromatic solvent.

The intermediate imine 20 is also prepared by condensing a 1-alkyl-5-oxo-5,6,7,8-tetrahydro-2(1H)-quinolinone 19 with primary amine 22 in the presence of titanium tetra-isopropoxide in a suitable solvent, for example, acetonitrile at a non-critical condensation temperature of about ambient temperature.

The reduction of the intermediate imine 20, generally conducted without purification, is effected by, for example, an alkali metal borohydride such as lithium borohydride, sodium borohydride, or potassium borohydride in an alkanol such as methanol, ethanol, or 1- or 2-propanol at about 0° to about 50° C. The preferred reduction conditions are sodium borohydride in ethanol at about 25° C.

Similarly, a tautomeric 5,6,7,8-tetrahydroquinolinone/5,6,7,8-tetrahydroquinoline 25a/25b is prepared by condensing a 2-aryalkyl-5-oxo-5,6,7,8-tetrahydroquinoline 23 wherein R is aryalkyl and $R^5$ and m are as before with a primary amine 22 to provide an imine 24 which is reduced and cleaved to a tautomeric 5-aminoquinoline 25a/25b, the process steps being performed by procedures substantially the same as those, for example, described hereinbefore for the respective conversions of 19 to 20 and 16 to 17a/17b.

By employing a secondary amine, i.e., an amine of formula 22 wherein neither $R^2$ or $R^3$ is hydrogen, and the procedures hereindescribed for the conversion of 19 to 21 and 23 to 25a/25b, one may construct a 5-(tertiary)-amino-5,6,7,8-tetrahydro-2(1H)-quinolinone 21 or a tautomeric 5-(tertiary)-amino-5,6,7,8-tetrahydroquinoline 25a/-quinolinone 25b.

By employing a aryloxyamine, i.e., a aryloxyamine of formula 22 wherein $R^2$ is hydrogen and $R^3$ is arylalkoxy and the processes for the conversion of 23 to 25a/25b, one can prepare an N-arylalkoxy-5,6,7,8-tetrahydroquinoline 27 wherein $R^8$ is arylalkyl via the intermediate oxime 26, which may be cleaved to a tautomeric primary amino-5,6,7,8-tetrahydroquinoline 25a/tetrahydroquinolinone 25b. In this approach, an O-arylalkylhydroxylamine is used in the form of its hydrohalide such as a hydrochloride in an alkanol such as ethanol in the presence of a weak base such as an alkali metal acetate, e.g., sodium acetate, at an elevated temperature of about the reflux temperature of the reaction medium, and the reduction is performed by an alkali metal cyanoborohydride such as sodium cyanoborohydride in an alkanoic acid such as acetic acid at a temperature of about 25° C. The cleavage of an O,N-diarylalkoxy-5,6,7,8-tetrahydroquinoline 27 to a tautomeric quinoline/quinolinone 25a/25b may be accomplished by following the directions for the cleavage of 7 to 8 and 8 to 1a/1b.

Still another approach to 5-amino-5,6,7,8-tetrahydroquinolines and related compounds involves acylation of a N,2-bis(arylalkoxy)-5,6,7,8-tetrahydro-5-quinolinamine 27 to an amide 28 which may be converted, for example, to a tautomeric quinolinol 1a/quinolinone 1b by processes hereinbeforedescribed. The acylation is accomplished by treating a 5-quinolinamine 27 with an alkanoic acid anhydride of formula 29

$(R^7CO)_2O$                      (29)

in a halocarbon solvent such as dichloromethane or trichloroethane, dichloromethane being preferred, in the presence of a promoter such as a N,N-dialkylaminopyridine, for example, N,N-dimethylpyridine at a reaction temperature of from about 0° to 50° C., a reaction temperature of about 25° C. being preferred.

In addition to the procedures outlined in R. Albrecht and E. Schröder, Arch. Pharmaz., 308,588 (1975) for the transformation of an N-unsubstituted quinolone 18 to a N-substituted, i.e., an N-alkyl, -alkenyl, or -phenylmethylquinolone 19, the conversion of 18 to 19 is performed by treating a quinolone 18 with a halide of formula 30

RHal                                     (30)

wherein R is alkyl, alkenyl, or phenylmethyl in an aprotic dipolar solvent such as dimethylacetamide, dimethylformamide, hexamethylphosphoramide, or dimethylsulfoxide in the presence of an alkali metal hydride such as lithium hydride, potassium hydride or sodium hydride at a condensation temperature of about 0° C. to about 50° C. The preferred reaction conditions are lithium hydride in dimethylformamide at a temperature of about 25° C.

Substituents on the 5-amino-5,6,7,8-tetrahydroquinolines of the present invention may be modified by conventional methods. For example, an alkenyl group of aminoquinolinone 21 wherein R is alkenyl is reduced by hydrogen in the presence of palladium-on-carbon in ethanol at atmospheric pressure to an aminoquinolinone 21 wherein R is alkyl.

The related compounds of the present invention may be prepared from the appropriate precursors by methods essentially the same as those hereinbeforedescribed.

The 5-amino-5,6,7,8-tetrahydroquinolines and related compounds of the present invention are useful as agents for the relief of memory dysfunction, particularly dysfunctions associated with decreased cholinergic activity such as those found in Alzheimer's disease. Relief of memory dysfunction activity of the instant compounds is demonstrated in the dark avoidance assay, an assay for the determination of the reversal of the effects of scopolamine induced memory deficits associated with decreased level of acetylcholine in the brain. In this assay, three groups of 15 male CFW mice were used, a vehicle/vehicle control group, a scopolamine/vehicle group, and a scopolamine/drug group. Thirty minutes prior to training, the vehicle/vehicle control group received normal saline subcutaneously, and the scopolamine/vehicle and scopolamine/drug groups received scopolamine subcutaneously (3.0 mg/kg, administered as scopolamine hydrobromide). Five minutes prior to training, the vehicle/vehicle control and scopolamine/vehicle groups received distilled water and the scopolamine/drug group received the test compound in distilled water.

The training/testing apparatus consisted of a plexiglass box approximately 48 cm long, 30 cm high and tapering from 26 cm wide at the top to 3 cm wide at the bottom. The interior of the box was divided equally by a vertical barrier into a light compartment (illuminated by 25-watt reflector lamp suspended 30 cm from the floor) and a dark compartment (covered). There was a hole at the bottom of the barrier 2.5 cm wide and 6 cm tall and a trap door which could be dropped to prevent an animal from passing between the two compartments. A Coulbourn Instruments small animal shocker was attached to two metal plates which ran the entire length of the apparatus, and a photocell was placed in the dark compartment 7.5 cm from the vertical barrier and 2 cm off the floor. The behavioral session was controlled by PDP 11/34 minicomputer.

At the end of the pretreatment interval, an animal was placed in the light chamber directly under the light fixture, facing away from the door to the dark chamber. The apparatus was then covered and the system activated. If the mouse passed through the barrier to the dark compartment and broke the photocell beam within 180 seconds, the trap door dropped to block escape to the light compartment and an electric shock was administered at an intensity of 0.4 milliamps for three seconds. The animal was then immediately removed from the dark compartment and placed in its home cage. If the animal failed to break the photocell beam within 180 seconds, it was discarded. The latency in seconds for each mouse was recorded.

Twenty-four hours later, the animals were again tested in the same apparatus except that no injections were made and the mice did not receive a shock. The test day latency in seconds for each animal was recorded and the animals were then discarded.

The high degree of variability (due to season of the year, housing conditions, and handling) found in one trial passive avoidance paradigm is well known. To control for this fact, individual cutoff (CO) values were determined for each test, compensating for interest variability. Additionally, it was found that 5 to 7% of the mice in the scopolamine/vehicle control groups were insensitive to scopolamine at 3 mg/kg, sc. Thus, the CO value was defined as the second highest latency time in the control group to more accurately reflect the 1/15 expected control responders in each test group. Experiments with a variety of standards repeated under a number of environmental conditions led to the development of the following empirical criteria: for a valid test, the CO value had to be less than 120 sec and the vehicle/vehicle control group had to have at least 5/15 animals with latencies greater than CO. For a compound to be considered active the scopolamine/compound group had to have at least 3/15 mice with latencies greater than CO.

The results of the dark avoidance test are expressed as the number of animals per group (%) in which this scopolamine induced memory deficit is blocked as measured by an increase in the latency period. Relief of memory dysfunction activity for representative compounds of the present invention is presented in the Table.

TABLE 1

| Compound | Dose (mg/kg, sc) | Percent of Animals with Scopolamine Induced Memory Deficit Reversal |
|---|---|---|
| N-(1,2,5,6,7,8-hexahydro-5-methyl-2-oxo-5-quinolinyl)acetamide | 0.16 | 20 |
| 1-methyl-5-[(2-phenyl-ethyl)amino]-5,6,7,8-tetrahydro-2(1H)-quinolinone | 1.0 | 33 |
| N-(phenylmethoxy)-N-[2-(phenylmethoxy)-5-5,6,7,8-tetrahydro-quinolinyl]acetamide | 1.0 | 20 |
| 5-[[2-(4-methoxyphenyl)ethyl]amino]-1-methyl-5,6,7,8-tetrahydro-2(1H)-quinolinone | 0.3 | 27 |
| 5-[[2-(3,4-dichloro-phenyl)-ethyl]amino]-1-methyl-5,6,7,8-tetra-hydro-2(1H)-quinolinone | 1.0 | 21 |
| physostigmine | 0.31 | 20 |

Relief of memory dysfunction activity is also demonstrated in the in vitro inhibition of actylcholinesterase activity, an assay for the determination of the ability of a drug to inhibit the inactivation of acetylcholine, a neurotransmitter implicated in the etiology of memory dysfunction and Alzheimer's dementia. In this assay, a modification of a test described by G. L. Ellman, et al., Biochem. Pharmacol., 7, 88 (1961), the following reagents are prepared and employed:

1. 0.05M Phosphate Buffer (pH 7.2)

A solution of monobasic sodium phosphate monhydrate (6.85 g) in distilled water (100 ml) is added to a solution of dibasic sodium phosphate heptahydrate (13.4 g) and distilled water (100 ml) until a pH of 7.2 was attained. The solution was diluted 1 to 10 with distilled water.

2. Substrate In Buffer

The 0.05M Phosphate Buffer (pH 7.2) was added to acetylthiocholine (198 mg) to a total volume of 100 ml, i.e., a quantity sufficient (gs) to 100 ml.

3. 5,5-Dithiobisnitrobenzoic Acid in Buffer

The 0.05M Phosphate Buffer (pH 7.2) was added to 5,5-dithiobisnitrobenzoic acid to a total volume of 100 ml, i.e., a quantity sufficient (gs) to 100 ml.

4. Stock Solution of Drug

A 2 millimolar stock solution of the test drug is prepared in a quantity sufficient of a suitable solvent, either acetic acid or dimethyl sulfoxide to volume with 5,5-Dithiobisnitrobenzene Acid in Buffer. Stock Solution of Drug is serially diluted (1:10) so that the final cuvette concentration is $10^{-4}$ molar.

Male Wistar rats are decapitated, brains rapidly removed, corpora strita dissected free, weighed and homogenized in 19 volumes (approximately 7 mg potein/ml) of 0.05M phosphate Buffer (pH 7.2) using a Potter-Elvehjem homogenizer. A 25 μl aliquot of this suspension is added to 1 ml of the vehicle or various concentrations of the test drug and preincubated for 10 minutes at 37° C. Enzyme activity is measured with a Beckman DU-50 spectrophotometer with the following software and instrument settings:

1. Kinetics Soft-Pac ™ Module #598273;
2. Program #6 Kindata;
3. Source—Vis;
4. Wavelength—412 nm;
5. Sipper—none;
6. Cuvettes—2 ml cuvettes using auto 6—sampler;
7. Blank—1 for each substrate concentration;
8. Interval time—15 seconds (15 or 30 seconds for kinetics);
9. Total time—5 minutes (5 or 10 minutes for kinetics);
10. Plot—yes;
11. Span—autoscale;
12. Slope—increasing;
13. Results—yes (gives slope); and
14. Factor—1.

Reagents are added to the blank and sample cuvettes as follows:

| 1. | Blank: | 0.8 ml 5,5-Dithiobisnitrobenzoic Acid |
| | | 0.8 ml Substrate in Buffer |
| 2. | Control: | 0.8 ml 5,5-Dithiobisnitrobenzoic Acid/ Enzyme |
| | | 0.8 ml Substrate in Buffer |

| | | |
|---|---|---|
| 3. | Drug: | 0.8 ml 5.5-Dithiobisnitrobenzoid Acid/ Drug/Enzyme |
| | | 0.8 ml Substrate in Buffer |

Blank values are determined for each run to control for non-enzymatic hydrolysis of substrate and these values are automatically subtracted by the Kindata program available on kinetics soft-pac module. This program also calculates the rate of absorbance change for each cuvette.

For $IC_{50}$ Determinations

Substrate concentration is 10 millimolar diluted 1:2 in assay yielding final concentration of 5 millimolar. 5,5-Dithiobisnitrobenzoic Acid concentration is 0.5 millimolar yielding 0.25 millimolar final concentration.

$$\% \text{ Inhibition} = \frac{\text{Slope Control} - \text{Slope drug}}{\text{Slope Control}} \times 100$$

$IC_{50}$ values are calculated from log-probit analysis

TABLE II

| Compounds | Inhibition of Acetylcholinesterase Activity $IC_{50}$ ($\mu M$) |
|---|---|
| 5-[[2-(4-chlorophenyl)ethyl]-amino]-5,6,7,8-tetrahydro-1-methyl-2(1H)-quinolinone | 6.6 |
| 5,6,7,8-tetrahydro-5-[[2-(4-methoxyphenyl)ethyl]amino]-1-methyl-2(1H)-quinolinone | 9.6 |
| 5-[[2-(3,4-dichlorophenyl)-ethyl]amino]-5,6,7,8-tetrahydro-1-methyl-2(1H)-quinolinone | 2.9 |
| 5,6,7,8-tetrahydro-5-[(2-phenylethyl)amino]-1-propyl-2(1H)-quinolinone fumarate | 3.1 |
| Physostigmine | 0.13 |

Memory deficit and scopolamine induced memory deficit reversal is achieved when the present 5-amino-5,6,7,8-tetrahydroquinolines and related compounds are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgement of the person administering or supervising the administration of the aforesaid compound. It is to be further understood that the dosages set forth herein are exemplary only and that they do not, to any extent, limit the scope or practice of the invention.

Included among the compounds of the present inventions are:

a. 5-[[2-(4-hydroxyphenyl)ethyl]amino-1-methyl-5,6,7,8-tetrahydro-2(1H)-quinolinone;

b. N-[2-methoxy-5,6,7,8-tetrahydro-5-quinolinyl]-N-methoxypropionamide;

c. 1-(2-phenylethyl)-5-(1-propoxyamino)-5,6,7,8-tetrahydro-2(1H)-quinolinone;

d. 1,5-dimethyl-5-(1-piperidinyl)-5,6,7,8-tetrahydro-2(1H)-quinolinone;

e. 2-hydroxy-5-methyl-5-(1-piperazinyl)-5,6,7,8-tetrahydroquinoline;

f. 1,5-dimethyl-5-(4-morpholinyl)-5,6,7,8-tetrahydro-2(1H)-quinolinone; and g. 2-hydroxy-5-methyl-5-(4-thiomorpholinyl-5,6,7,8-tetrahydroquinoline.

h. 1,5-dimethyl-5-[3-(propynyl)amino]-5,6,7,8-tetrahydro-2(1H)-quinolinone.

i. 5-amino-1,5,6,7-tetrahydro-1,5-dimethyl-2H-1-pyridin-2-one.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

5,6,7,8-Tetrahydro-5-oxo-2-(phenylmethoxy)quinoline

A suspension of 5,6,7,8-tetrahydro-5-oxo-2(1H)-quinolinone (33.0 g), silver carbonate (35.0 g), benzyl bromide (44.4 g), and toluene (400 ml) was stirred at room temperature for 72 hrs. The mixture was filtered and the filtrate was concentrated. Trituration of the residue with petroleum ether gave 45.6 g (83%) of product.

EXAMPLE 2

5,6,7,8-Tetrahydro-5-hydroxy-5-methyl-2-(phenylmethoxy)quinoline

Methylmagnesium bromide (3.0M in diethyl ether, 47 ml) was added dropwise to a solution of 5,6,7,8-tetrahydro-5-oxo-2-(phenylmethoxy)quinoline (29.6 g) and toluene (1l) at 0° C. The reaction mixture was allowed to warm to room temperature, with stirring. The reaction mixture was then quenched with saturated ammonium chloride solution, the layers were separated, and the aqueous phase was extracted with ethyl acetate. The combined organic layers were washed with brine, dried over anhydrous magnesium sulfate, filtered, and the filtrate was concentrated to provide 31.7 g (92.0%) of product.

EXAMPLE 3

5,6,7,8-Tetrahydro-5-methyl-2-(phenylmethoxy)-5-quinolinamine hemifumarate

Trifluoroacetic acid (17.4 g) was added in one portion to a solution of 5,6,7,8-tetrahydro-5-methyl-2-(phenylmethoxy)-quinolin-5-ol (41 g), phenylmethoxyamine (47 g), and toluene (770 ml) at room temperature. The solution was stirred at room temperature for 24 hrs, and then quenched with concentrated ammonium hydroxide solution. The layers were separated and the aqueous phase was extracted with ethyl acetate. The combined organic layers were washed with brine, dried over potassium carbonate, filtered, and the filtrate was concentrated. Purification by high performance liquid chromatography (silica gel, elution with ethyl acetate-hexanes) gave 44.2 g (77%) of 5,6,7,8-tetrahydro-5-methyl-N,2-bis(phenylmethoxy)-5-quinolinamine.

A portion of the 5,6,7,8-tetrahydro-5-methyl-N,2-bis(phenylmethoxy)-quinolinamine (30.3 g) in tetrahydrofuran (120 ml) was treated dropwise with borane-tetrahydrofuran complex (1M in tetrahydrofuran, 243 ml) at 0° C. The solution was heated under reflux for 2 hrs, cooled to 0° C., and water (30 ml) was added. The mixture was concentrated in vacuo, 20% potassium hydroxide solution (50 ml) was added, and the mixture was heated under reflux for 1.5 hrs. The mixture was cooled, acidified with 6N hydrochloric acid and washed with diethyl ether. The aqueous phase was basified with potassium hydroxide solution and the mixture was extracted with dichloromethane. The combined organic layers were washed with brine, dried over anhydrous magnesium sulfate, filtered, and the filtrate was concentrated.

A 2.9 g-portion of the residue (19.6 g) was dissolved in ethyl acetate, and the solution was treated with an equivalent amount of fumaric acid. The precipitate was collected; yield 2.68 g (68%) of product, mp 189°–190° C.

ANALYSIS: Calculated for $C_{19}H_{22}N_2O_3$: 69.92% C, 6.79% H, 8.58% N. Found: 69.59% C, 6.73% H, 8.55% N.

EXAMPLE 4

5,6,7,8-Tetrahydro-5-amino-5-methyl-2(1H)-quinolinone hydrochloride 5,6,7,8-Tetrahydro-5-methyl-2-(phenylmethoxy)-5-quinolinamine dihydrochloride (9.5 g) and 10% palladium-on-carbon (730 mg) in absolute ethanol (500 ml) were shaken on a Parr hydrogenation apparatus, starting at 55 psi of hydrogen, until hydrogen uptake ceased. The catalyst was removed by filtration, and the filtrate was neutralized with 4-polyvinylpyridine and concentrated. The residue was suspended in hot methanol and the solid was collected. The solid was combined with the material that crystallized from the methanol to afford 3.36 g (56%) of product, mp 214°–216° C. (dec).

ANALYSIS: Calculated for $C_{10}H_{15}N_2O$: 55.94% C, 7.04% H, 13.05% N. Found: 55.71% C, 7.02% H, 12.91% N.

EXAMPLE 5

5,6,7,8-Tetrahydro-5-amino-1,5-dimethyl-2(1H)-quinolinone

A mixture of sodium hydride (50% in oil, 2.9 g), 5-amino-5,6,7,8-tetrahydro-5-methyl-2(1H)-quinolinone hydrochloride (5.43 g), and dimethylformamide (370 ml) was stirred at room temperature for 1.5 hrs. Methyl iodide (3.97 g) was added, and the mixture was allow to stand at room temperature for 20 hrs. The reaction mixture was concentrated in vacuo, and the residue was washed with dichloromethane. The washings were concentrated, the residue was dissolved in a mixture of ethyl acetate and methanol and treated with 0.5 equivalents of fumaric acid. The precipitate (2.65 g) was combined with a 1.9 g-sample obtained in another experiment, and the combined material was treated with 5% sodium hydroxide solution and extracted with dichloromethane. The extract was concentrated. Recrystallization of the residue from ethyl acetate gave 2.1 g (23%) of product, mp 166–167.5 C.

ANALYSIS: Calculated for $C_{11}H_{16}N_2O$: 68.72% C, 8.39% H, 14.57% N. Found: 68.68% C, 8.37% H, 14.52% N.

EXAMPLE 6

N,2-Bis(phenylmethoxy)-5,6,7,8-tetrahydro-N,5-dimethyl-5-quinolinamine

Methyllithium (1.4M in diethyl ether, 37.7 ml) was added dropwise over 20 min to a solution of N,2-bis(phenylmethoxy)-5,6,7,8-tetrahydro-5-methyl-5-quinolinamine (18.1 g) and tetrahydrofuran (20 ml) at −78° C. The mixture was allowed to warm to room temperature over 2 hrs and was stirred at room temperature for an additional 1 hr. The solution was quenched with saturated ammonium chloride solution and extracted with ethyl acetate. The combined organic layers were washed with brine, dried over anhydrous potassium carbonate, filtered, and the filtrate was concentrated. The residue was purified by high performance liquid chromatography (silica gel, elution with ethyl acetate-hexanes) to provide 12.3 g (65%) of product.

EXAMPLE 7

5,6,7,8-Tetrahydro-N,5-dimethyl-2-(phenylmethoxy)-5-quinolinamine 5,6,7,8-Tetrahydro-N,5-dimethyl-N,2-bis(phenylmethoxy)-5-quinolinamine (12.3 g) in tetrahydrofuran (160 ml) at 0° C. was treated dropwise with borane-tetrahydrofuran complex (1M in tetrahydrofuran, 63.4 ml). The solution was heated under reflux for 3 hrs, cooled to 0° C., and water (30 ml) was added. The reaction mixture was concentrated in vacuo, 20% potassium hydroxide solution (60 ml) was added, and the mixture was heated at reflux for 2 hrs. The mixture was cooled, acidified with conc hydrochloric acid, and washed with diethyl ether. The aqueous phase was basified with 20% potassium hydroxide solution and extracted with dichloromethane. The combined organic layers were washed with brine, dried over potassium carbonate, filtered, and the filtrate was concentrated to afford 6.3 g (92%) of product.

EXAMPLE 8

5,6,7,8-Tetrahydro-5-methyl-5-(methylamino)-2(1H)-quinolinone hydrochloride 5,6,7,8-Tetrahydro-N,5-dimethyl-2-(phenylmethoxy)-5-quinolinamine (6.3 g) in ethanol (500 ml) was acidified to ca pH2 with a solution of hydrochloric acid in 2-propanol. 10% Palladium-on-carbon (315 mg) was added and the mixture was shaken on Parr hydrogenation apparatus, starting at 55 psi of hydrogen, until hydrogen uptake ceased. The catalyst was collected and the filtrate was neutralized with 4-polyvinylpyridine. The solution was concentrated in vacuo to a volume of about 75 ml and diethyl ether was added. The precipitate was collected and recrystallized first from methanol and then from water/2-propanol to afford 1.3 g (25%) of product, mp 190°–195° C. (dec).

ANALYSIS: Calculated for $C_{11}H_{17}ClN_2O$: 57.77% C, 7.49% H, 12.25% N. Found: 57.36% C, 7.46% H, 12.11% N.

EXAMPLE 9

5,6,7,8-Tetrahydro-5-hydroxy-2-(phenylmethoxy)-5-(phenylmethyl)quinoline

Benzylmagnesium chloride (1.0M in diethyl ether, 175 ml) was added dropwise to a solution of 5,6,7,8-tetrahydro-5-oxo-2-(phenylmethoxy)quinolinone (37.0 g) and 1.4 l of toluene at 0° C. The mixture was allowed to warm to room temperature and saturated ammonium chloride solution was added. The layers were separated and the aqueous phase was extracted with ethyl acetate. The combined organic layers were washed with brine, dried over anhydrous magnesium sulfate, filtered, and the filtrate was concentrated to provide 50.0 g of product.

EXAMPLE 10

5,6,7,8-Tetrahydro-2-(phenylmethoxy)-5-(phenylmethyl)-5-quinolinamine

Trifluoroacetic acid (16.6 g) was added in one portion to a solution of 5,6,7,8-tetrahydro-5-hydroxy-2-(phenylmethoxy)-5-(phenylmethyl)quinoline (50 g), phenylmethoxyamine (44.8 g), and toluene (600 ml) at room temperature. The solution was stirred at room temperature for 19 hrs, and the reaction mixture was quenched with conc ammonium hydroxide solution. The layers were separated and the aqueous phase was extracted with ethyl acetate. The combined organic layers were washed with brine, dried over potassium carbonate, filtered, and the filtrate was concentrated. Purification by high performance liquid chromatography (silica gel, elution with ethyl acetate-hexanes) gave 40.0 g (61%) of 5,6,7,8-tetrahydro-N,2-bis(phenylmethoxy)-5-(phenylmethyl)-5-quinolinamine.

5,6,7,8-Tetrahydro-N,2-bis(phenylmethoxy)-5-(phenylmethyl)-5-quinolinamine (40.0 g) in tetrahydrofuran (90 ml) was treated dropwise with borane-tetrahydrofuran complex (1M in tetrahydrofuran, 267 ml) at 0° C. The solution was heated under reflux for 3 hrs, cooled to 0° C. and water (30 ml) was added. The reaction mixture was concentrated in vacuo, 20% potassium hydroxide solution (60 ml) was added, and the mixture was heated under reflux for 8 hours. The mixture was cooled, acidified with conc hydrochloric acid, and washed with diethyl ether. The aqueous phase was basified with 20% potassium hydroxide solution and extracted with dichloromethane. The combined organic layers were washed with brine, dried over potassium carbonate, filtered, and the filtrate was concentrated to afford 19.1 g (37.0%) of product.

EXAMPLE 11

5-Amino-5,6,7,8-tetrahydro-5-(phenylmethyl)-2(1H)-quinolinone hydrochloride

A mixture of 5,6,7,8-tetrahydro-5-(phenylmethyl)-2-(phenylmethoxy)-5-quinolinamine (19.1 g) and 10% palladium-on-carbon (1.5 g) in ethanol (1 l) was acidified to about pH 2–3 with 2propanol/hydrochloric acid solution. The mixture was shaken on Parr hydrogenation apparatus, starting at 55 psi of hydrogen, until hydrogen uptake ceased. The catalyst was removed by filtration, the filtrate was neutralized with 4-polyvinylpyridine and concentrated. The residue was triturated with a mixture of methanol and ethyl acetate. The precipitate was collected and recrystallized form water/methanol/ethyl acetate to afford 4.6 g (28%) of product, mp 235°–238° C. (dec), in two crops.

ANALYSIS: Calculated for $C_{16}H_{19}ClN_2O$: 66.09% C, 6.59% H, 9.63% N. Found: 65.83% C, 6.68% H, 9.56% N.

EXAMPLE 12

N-[5,6,7,8-Tetrahydro-5-methyl-2-(phenylmethoxy)-5-quinolinyl]acetamide

Conc sulfuric acid (70 ml) was added dropwise over 45 mins to a solution of 5,6,7,8-tetrahydro-5-hydroxy-5-methyl-2-(phenylmethoxy)quinoline (14.0 g) and acetonitrile (200 ml) at 0° C. The solution was stirred at room temperature for 18 hrs, poured over ice, and basified to pH 8 with 50% sodium hydroxide solution. The aqueous phase was extracted with ethyl acetate, and the combined organic layers were washed with brine, dried over anhydrous magnesium sulfate, filtered, and the filtrate was concentrated. The residue was purified by colmn chromatography (silica gel, elution with ethyl acetate). The appropriate fractions were collected and evaporated. Recrystallization (twice) of the residue from ethyl acetate/hexanes gave 2.60 g (16%) of product, mp 153°–154° C.

ANALYSIS: Calculated for $C_{19}H_{22}N_2O_2$: 73.52% C, 7.14% H, 9.02% N. Found: 73.88% C, 7.12% H, 9.02% N.

EXAMPLE 13

N-(1,2,5,6,7,8-Hexahydro-5-methyl-2-oxo-5-quinolinyl)acetamide 5,6,7,8-Tetrahydro-N-[5-methyl-2-(phenylmethoxy)-5-quinolinyl]acetamide hydrochloride (4.5 g) and 10% palladium-on-carbon (225 mg) in absolute ethanol (250 ml) were shaken on a Parr hydrogenation apparatus at an initial pressure of 55 psi of hydrogen, until hydrogen uptake ceased. The catalyst was removed by filtration, the filtrate was neutralized with 4-polyvinylpyridine, and the mixture was concentrated. The residue was combined with a 1.79 g sample obtained in another experiment. Recrystallization from absolute ethanol gave 2.81 g (60%) of product, mp 235°–237° C. (dec).

ANALYSIS: Calculated for $C_{12}H_{16}N_2O_2$: 65.43% C, 7.32% H, 12.72% N. Found: 65.02% C, 7.27% H, 12.54% N.

EXAMPLE 14

5,6,7,8-Tetrahydro-5-[-(2-phenylethyl)amino]-2(1H)-quinolinone hydrochloride

A mixture of phenethylamine (5.0 g), 5,6,7,8-tetrahydro-2-(phenylmethoxy)-5-oxoquinoline (10.0 g), and a catalytic amount of para-toluenesulfonic acid (206 mg) was heated under reflux in toluene (200 ml) with azeotropic removal of water for 36 hrs. The solution was cooled and washed with water. The aqueous phase was extracted with dichloromethane, and the combined organic layers were washed with brine, dried over anhydrous magnesium sulfate, filtered, and the filtrate was concentrated. Sodium borohydride (1.4 g) was added to a solution of the residue and ethyl alcohol (125 ml) and the mixture was stirred at room temperature for 3 hrs. The reaction mixture was concentrated in vacuo, the residue was quenched with water, and the mixture was extracted with ethyl acetate. The combined organic layers were washed with brine, dried over anhydrous magnesium sulfate, filtered, and the filtrate was concentrated to afford 12.5 g (92%) of 5,6,7,8-tetrahydro-5-(2-phenethylamino)-2-(phenylmethoxy)quinoline.

5,6,7,8-Tetrahydro-5-(2-phenethylamino)-2-(phenylmethoxy)quinoline (12.5 g) was converted into its hydrochloride. The hydrochloride and 10% palladium-on-carbon (830 mg) in methanol (1l) were shaken on a Parr hydrogenation apparatus, starting at 55 psi of hydrogen, until hydrogen uptake ceased. The catalyst was removed by filtration, the filtrate was neutralized with 4-polyvinylpyridine, and concentrated. Recrystallization of the residue from methanol/ethyl acetate afforded 2.68 g of product, mp 200°–202° C. (dec). An additional 2.2 g of product was obtained from the other liquors; overall yield 42%.

ANALYSIS: Calculated for $C_{17}H_{21}ClN_2O$: 66.99% C 6.94% H, 9.19% N. Found: 66.85% C, 6.96% H, 9.12% N.

EXAMPLE 15

5,6,7,8-Tetrahydro-1-methyl-5-[(2-phenylethyl)amino]-2(1H)-quinolinone dihydrochloride monohydrate A mixture of phenethylamine (6.0 g), 5,6,7,8-tetrahydro-1-methyl-5-oxo-2(1H)-quinolinone (8.0 g) and a catalytic amount of para-toluenesulfonic acid was heated in toluene (90 ml) under reflux for 18 hrs, with azeotropic removal of water. The solution was cooled and washed with water. The aqueous phase was extracted with dichloromethane. The combined organic layers were washed with brine, dried over anhydrous magnesium sulfate, filtered, and the filtrate was concentrated. The residue was washed with hexanes and the solvent was decanted. Sodium borohydride (0.82 g) was added to a solution of the residue in ethyl alcohol (160 ml) and the mixture was stirred at room temperature for 0.5 hr. The reaction mixture was concentrated in vacuo, the residue was quenched with water, and the mixture was extracted with ethyl acetate. The combined organic extracts were washed with brine, dried over anhydrous magnesium sulfate, filtered, and the filtrate was concentrated. The residue was dissolved in methanol and treated with ethereal hydrogen chloride. The mixture was concentrated in vacuo and the residue was dissolved in ethanol. Ethyl acetate was added, the precipitate was collected, and the precipitate was recrystallized twice from ethanol-ethyl acetate to afford 4.0(24%) of product, mp 163°–166° C.(softens at 142° C.).

ANALYSIS: Calculated for $C_{18}H_{26}Cl_2N_2O_2$: 57.91% C, 7.02% H, 7.50% N. Found: 57.97% C, 6.93% H, 7.47% N.

EXAMPLE 16

5,6,7,8-Tetrahydro-N,2-bis(phenylmethoxy)-5-quinolinamine 5,6,7,8-Tetrahydro-5-oxo-2-(phenylmethoxy)-quinoline(20 g), O-benzylhydroxylamine hydrochloride (19 g), and sodium acetate (9.8 g) in a 1/1-mixture of ethanol and water (200 ml) were heated under reflux for 3 hrs. The solvent was decanted and the residue was purified by high performance liquid chromatography (silica gel, elution with 5% ethyl acetate/hexanes). The appropriate fractions were collected and evaporated to give 21.5(76%) of 5,6,7,8-tetrahydro-5-oxo-2-(phenylmethoxy)quinoline oxime benzyl ether.

5,6,7,8-Tetrahydro-5-oxo-2-(phenylmethoxy)quinoline oxime benzyl ether (20.3 g) in acetic acid (280 ml) was treated with sodium cyanoborohydride (14.2 g) at room temperature. After 16 hrs, the mixture was cooled to 0° C. and acidified with 6N hydrochloric acid. The reaction mixture was concentrated in vacuo. The residue was dissolved in water, basified with potassium hydroxide solution, and the mixture was extracted with dichloromethane. The combined organic layers were dried over anhydrous magnesium sulfate, filtered, and the filtrate was concentrated. The residue was purified by high performance liquid chromatography (silica gel, elution with 20% ethyl acetate/hexanes). The appropriate fractions were collected and evaporated to give 12.0 g (60%) of product.

EXAMPLE 17

N-(Phenylmethoxy)-N-[5,6,7,8-tetrahydro-2-(phenylmethoxy)-5-quinolinyl]acetamide hydrochloride Acetic anhydride (3.77 g) was added to a solution of N,N-dimethylaminopyridine (0.2 g), N,2-bis(phenylmethoxy)-5,6,7,8-tetrahydro-5-quinolinamine (12.1 g) and dichloromethane (170 ml) at room temperature. The mixture was stirred at room temperature for 48 hrs, diluted with dichloromethane, and extracted with saturated sodium bicarbonate solution. The combined extracts were washed with water, brine, dried over anhydrous magnesium sulfate, filtered, and the filtrate was concentrated. The residue was dissolved in methanol and acidified with 2-propanol/hydrochloric acid solution. The mixture was evaporated and the residue was recrystallized from ethanol/ethyl acetate to give 7.64 g (52%) of product, mp 125°–126° C.

ANALYSIS: Calculated for $C_{25}H_{27}ClN_2O_3$: 68.41% C, 6.20% H, 6.38% N. Found: 68.33% C, 6.20% H, 6.37% N.

EXAMPLE 18

5,6,7,8-Tetrahydro-5-[(2-phenylethyl)amino]-1-(2-propenyl)-2(1H)-quinolinone

A mixture of 5,6,7,8-tetrahydro-5-oxo-2(1H)-quinolinone (20.0 g), lithium hydride (1.57 g), and dimethylformamide (800 ml) was stirred for 3 hrs at 25° C., under nitrogen. 3-Bromopropene (15.5 g) was added and the mixture was stirred for an additional eighteen hrs. The reaction mixture was concentrated and the residue was partitioned between ethyl acetate and water. The layers were separated and the aqueous layer was extracted with ethyl acetate. The combined organic extracts were washed with water and brine, dried over anhydrous magnesium sulfate, filtered, and the filtrate was concentrated. The residue was triturated with petroleum ether to afford 15.7 g (63%) of 5,6,7,8-tetrahydro-5-oxo-1-(2-propenyl)-2(1H)-quinolinone.

A mixture of phenethylamine (6.1 g), 5,6,7,8-tetrahydro-5-oxo-1-(2-propenyl)-2(1H)-quinolinone (10.0 g), and a catalytic amount of para-toluenesulfonic acid was heated in refluxing toluene (150 ml), with azeotropic removal of water, for 18 hrs. The solution was cooled and washed with water. The aqueous phase was extracted with dichloromethane, and the combined organic layers were washed with brine, dried over anhydrous magnesium sulfate, filtered, and the filtrate was concentrated. Sodium borohydride (1.8 g) was added to the residue in ethyl alcohol (150 ml) and the resulting mixture was stirred at room temperature for 0.5 hr. The mixture was concentrated in vacuo, and the residue was quenched with water. The mixture was extracted with ethyl acetate. The combined organic layers were washed with brine, dried over anhydrous magnesium sulfate, filtered, and the filtrate was concentrated. The residue was purified by high performance liquid chromatography (silica gel, eluted with methanol/ethyl acetate) to afford 13.6 g (89%) of product. Recrystallization from diethyl ether/petroleum ether provided the analytical sample, mp 60°–62° C.

ANALYSIS:
Calculated for $C_{20}H_{24}N_2O$: 77.89% C, 7.84% H, 9.08% N. Found: 78.06% C, 7.65% H, 9.10% N.

EXAMPLE 19

5-[[2-(3,4-Dichlorophenyl)ethyl]amino]-5,6,7,8-tetrahydro-1-(2-propenyl)-2(1H)-quinolinone fumarate A mixture of 2-(3,4-dichlorophenyl)ethylamine (3.8 g), 5,6,7,8-tetrahydro-5-oxo-1-(2-propenyl)-2(1H)-quinolinone (3.0 g), and para-toluenesulfonic acid (225 mg) was heated in refluxing toluene (50 ml), with azeotropic removal water, for 24 hrs. An additional 1 g of the amine was added, and the mixture was heated for an additional 24 hrs. The solution was cooled, and the mixture was concentrated in vacuo. Sodium borohydride (0.56 g) was added to a solution of the residue in ethyl alcohol (50 ml), and the resulting mixture was stirred at room temperature for 1 hr. The mixture was concentrated in vacuo, and the residue was quenched with water. The mixture was extracted with dichloromethane. The combined organic layers were washed with brine, dried over anhydrous magnesium sulfate, filtered, and the filtrate was concentrated. The residue was purified by high performance liquid chromatography (silica gel, eluted with 5% methanol/ethyl acetate) to provide 4.03 g (73%) of basic product. The product was dissolved in ethanol, treated with an equivalent amount of fumaric acid, and the mixture was concentrated in vacuo. The residue was recrystallized from ethanol to provide the analytical sample, mp 160°–161° C.

ANALYSIS: Calculated for $C_{24}H_{26}Cl_2N_2O_5$: 58.43% C, 5.31% H, 5.68% N. Found: 58.41% C, 5.61% H, 5.67% N.

EXAMPLE 20

5,6,7,8-Tetrahydro-5-[(2-phenylethyl)amino]-1-propyl-2(1H)-quinolinone fumarate

A mixture of 5,6,7,8-tetrahydro-5-[(2-phenylethyl)amino]-(2-propenyl)-2(1H)-quinolinone (4.68 g) and 10% palladium-on-carbon (0.47 g) in ethanol (100 ml) was stirred under hydrogen at atmospheric pressure for 3 hrs. The mixture was filtered through celite, and the filtrate was concentrated. The residue solidified upon standing. The solid was dissolved in ethanol and treated with an equivalent amount of fumaric acid. The mixture was evaporated, and the residue was recrystallized twice, first from ethanol/ethyl acetate, and then from ethanol to provide 4.63 g (71%) of product, mp 151°–153° C.

ANALYSIS: Calculated for $C_{24}H_{30}N_2O_5$: 67.59% C, 7.09% H, 6.57% N. Found: 67.61% C, 7.09% H, 6.59% N.

EXAMPLE 21

5-[[2-(3,4-Dichlorophenyl)ethyl]amino]-5,6,7,8-tetrahydro-1-(phenylmethyl)-2(1H)-quinolinone fumarate A mixture of 5,6,7,8-tetrahydro-5-oxo-2(1H)-quinolinone (5.0 g), lithium hydride (0.37 g), and dimethylformamide (200 ml) was stirred at 25° C. for 3 hrs. Benzyl bromide (5.5 g) was added and the mixture was stirred for 20 hrs. Water was added, and the mixture was concentrated under reduced pressure. The residue was partitioned between ethyl acetate and water. The layers were separated and combined organic phase was washed with water, brine, dried over anhydrous magnesium sulfate, filtered, and the filtrate was concentrated. The residue was triturated with hexanes to provide 4.5 (58%) of 5,6,7,8-tetrahydro-5-oxo-1-phenylmethyl-2(1H)-quinolinone.

A mixture of 2-(3,4-dichlorophenyl)ethylamine (2.7 g), 5,6,7,8-tetrahydro-5-oxo-1-phenylmethyl-2(1H)-quinolinone (3.0 g), and para-toluenesulfonic acid (180 mg) was heated in 50 ml of refluxing toluene, with azeotropic removal of water, for 25 hrs. An additional 1 g of the amine was added, and the mixture was heated for an additional 63 hrs. The solution was cooled and concentrated in vacuo. Sodium borohydride (0.45 g) was added to a solution of the residue in ethyl alcohol (50 ml), and the mixture was stirred at room temperature for 1 hr. The mixture was concentrated in vacuo, the residue was quenched with water, and the product was extracted with dichloromethane. The combined organic layers were washed with brine, dried over anhydrous magnesium sulfate, filtered, and the filtrate was concentrated. The residue was purified by high performance liquid chromatography (silica gel, eluted with methanol/ethyl acetate) to afford 4.0 g (80%) of basic product. The basic product was dissolved in hot ethanol and treated with an equivalent amount of fumaric acid. The solvent was removed and the residue was recrystallized from ethanol/ethyl acetate to provide 3.0 g of the analytical sample, mp 176°–178° C.

ANALYSIS: Calculated for $C_{28}H_{28}Cl_2N_2O_5$: 61.88% C, 5.19% H, 5.15% N. Found: 61.59% C, 5.16% H, 5.07% N.

EXAMPLE 22

5,6,7,8-Tetrahydro-1-methyl-5-[(phenylmethyl)amino]-2(1H)-quinolinone fumarate

A mixture of benzylamine (2.2 g), 5,6,7,8-tetrahydro-1-methyl-5-oxo-2(1H)-quinolinone (3.0 g), and para-toluenesulfonic acid (0.13 g) was heated in refluxing toluene (50 ml), with azeotropic removal of water, for 40 hrs. An additional 0.98 g of amine and 0.1 g of para-toluenesulfonic acid were added. The reaction mixture was heated under reflux for an additional 24 hrs, and then cooled. The mixture was concentrated in vacuo. Sodium borohydride (0.6 g) was added to a solution of the residue in ethyl alcohol (50 ml), and the mixture was stirred at room temperature for 1 hr. The mixture was concentrated in vacuo, the residue was quenched with water, and the mixture was extracted with dichloromethane. The combined organic layers were washed with brine, dried over anhydrous magnesium sulfate, filtered, and the filtrate was concentrated. The residue was purified by high performance liquid chromatography (silica gel, eluted with methanol/ethyl acetate) to give 3.1 g (69%) of basic product. The basic product was dissolved in ethanol and treated with 1.34 g of fumaric acid to give the fumarate, mp 159°–161° C.

ANALYSIS: Calculated for $C_{21}H_{24}N_2O_5$: 65.61% C, 6.29% H, 7.29% N. Found 65.23% C, 6.32% H, 7.11% N.

EXAMPLE 23

5-[[2-(4-Trifluoromethylphenyl)ethyl]amino]-5,6,7,8-tetrahydro-1-methyl-2(1H)-quinolinone A mixture of 2-(4-trifluoromethylphenyl)ethylamine (4.1 g), 5,6,7,8-tetrahydro-1-methyl-5oxo-2(1H)-quinolinone (3.0 g), and para-toluenesulfonic acid (256 mg) was heated in refluxing toluene (50 ml), with azeotropic removal or water, for 40 hrs. An additional 2.0 g of the amine was added and the mixture was refluxed for 36 hr. The solution was cooled, and the mixture was concentrated in vacuo. Sodium borohydride (0.6 g) was added to a solution of the residue in ethyl alcohol (50 ml), and the resulting mixture was stirred at room temperature for 1 hr. The mixture was concentrated in vacuo, the residue was quenched with water, and the mixture was extracted with dichloromethane. The combined organic layers were washed with brine, dried over anhydrous magnesium sulfate, filtered, and the filtrate was concentrated. The residue was recrystallized from ethyl acetate/hexanes to provide, in two crops, 3.8 g (65%) of product, mp 104°–106° C.

ANALYSIS: Calculated for $C_{19}H_{21}F_3N_2O$: 65.13% C, 6.04% H, 7.99% N. Found: 65.13% C, 6.16% H, 7.97% N.

EXAMPLE 24

5,6,7,8-Tetrahydro-1-methyl-5-[[2-(4-nitrophenyl)ethyl]amino]-2(1H)-quinolinone

A mixture of 2-(4-nitrophenyl)ethylamine (3.4 g), 5,6,7,8-tetrahydro-1-methyl-5-oxo-2(1H)-quinolinone (3.0 g), and para-toluenesulfonic acid (256 mg) was heated in refluxing toluene (70 ml), with azeotropic removal of water, for a total of 72 hrs. An additional 1.0 g of the amine was added at 24 and 48 hrs. The resulting solution was cooled and concentrated in vacuo. Sodium borohydride (0.6 g) was added to a solution of the residue in ethyl alcohol (70 ml). The resulting mixture was stirred at room temperature for 1 hr, and the mixture was concentrated in vacuo. The residue was quenched with water, and the mixture was extracted with dichloromethane. The combined organic layers were washed with brine, dried over anhydrous magnesium sulfate, filtered, and the filtrate concentrated. The residue was purified by high performance liquid chromatography (silica gel, eluted with methanol/ethyl acetate) to provide 3.8 g (69%) of product. Recrystallization from ethyl acetate afforded the analytical sample, mp 138°–139° C., ANALYSIS: Calculated for $C_{18}H_{21}N_3O_3$: 66.04% C, 6.47% H, 12.84% N. Found: 65.82% C, 6.19% H, 12.66% N.

EXAMPLE 25

5-[[2-(4-Chlorophenyl)ethyl]amino]-5,6,7,8-tetrahydro-1-methyl-2(1H)-quinolinone A mixture of 2-(4-chlorophenyl)ethylamine (5.8 g), 5,6,7,8-tetrahydro-1-methyl-5-oxo-2(1H)-quinolinone (5.5 g), and a catalytic amount of para-toluenesulfonic acid was heated in refluxing toluene (90 ml), with azeotropic removal of water, for 40 hrs. The solution was cooled and concentrated in vacuo. Sodium borohydride (1.1 g) was added to a solution of the residue in ethyl alcohol (90 ml), and the mixture was stirred at room temperature for 2 hrs. The mixture was concentrated in vacuo, the residue was quenched with water, and the mixture was extracted with dichloromethane. The combined organic layers were washed with brine, dried over anhydrous magnesium sulfate, filtered, and the filtrate was concentrated. Recrystallization of the residue from ethyl acetate/hexanes provided 6.55 g (67%) of product, mp 110°–112° C.

ANALYSIS: Calculated for $C_{18}H_{21}N_2O$: 68.24% C, 6.68% H, 8.84% N. Found: 68.36% C, 6.74% H, 8.78% N.

EXAMPLE 26

5,6,7,8-Tetrahydro-5-[[2-(4-methoxyphenyl)ethyl]amino]-1-methyl-2(1H)-quinolinone A mixture of 2-(4-methoxyphenyl)ethylamine (5.6 g), 5,6,7,8-tetrahydro-1-methyl-5-oxo-2(1H)-quinolinone (5.5 g), and a catalytic amount of para-toluenesulfonic acid was heated in refluxing toluene (90 ml), with azeotropic removal of water, for 39 hrs. The solution was cooled and concentrated in vacuo. Sodium borohydride (1.1 g) was added to a solution of the residue in ethyl alcohol (90 ml), and the mixture was stirred at room temperature for 2 hrs. The mixture was concentrated in vacuo, the residue was quenched with water, and the mixture was extracted with dichloromethane. The combined organic layers were washed with brine, dried over anhydrous magnesium sulfate, filtered, and the filtrate was concentrated. The residue was washed with diethyl ether to afford 7.8 g (81%) of product. Recrystallization from ethyl acetate/hexanes provided the analytical sample, mp 97°–99° C.

ANALYSIS: Calculated for $C_{19}H_{24}N_2O_2$: 73.05% C, 7.74% H, 8.97% N. Found: 73.38% C, 7.48% H, 9.01% N.

EXAMPLE 27

5,6,7,8-Tetrahydro-1-methyl-5-[[2-(4-methylphenyl)ethyl]amino]-2(1H)-quinolinone fumarate A mixture of 2-(4-methylphenyl)ethylamine (2.7 g), 5,6,7,8-tetrahydro-1-methyl-5-oxo-2(1H)-quinolinone (3.0 g), and para-toluenesulfonic acid (0.13 g) was heated in refluxing toluene (50 ml), with azeotropic removal of water, for 42 hrs. The mixture was cooled and concentrated in vacuo. Sodium borohydride (0.64 g) was added to a solution of the residue in 50 ml of ethyl alcohol, and the mixture was stirred at room temperature for 1 hr. The mixture was concentrated in vacuo, the residue was quenched with water, and the mixture was extracted with dichloromethane. The combined organic layers were washed with brine, dried over anhydrous magnesium sulfate, filtered, and the filtrate was concentrated. The residue was dissolved in ethanol, treated with 1.9 g of fumaric acid, and the salt was allowed to crystallize. Recrystallization from ethanol/2-isopropyl ether gave 3.87 g (56%) of product, mp 158°–161° C.

ANALYSIS: Calculated for $C_{23}H_{28}N_2O_5$: 66.97% C, 6.84% H, 6.79% N. Found: 67.05% C, 6.88% H, 6.78% N.

EXAMPLE 28

5-[[2-(2,4-Dichlorophenyl)ethyl]amino]-5,6,7,8-tetrahydro-1-methyl-2(1H)-quinolinone A mixture of 2-(2,4-dichlorophenyl)ethylamine (3.8 g), 5,6,7,8-tetrahydro-1-methyl-5-oxo-2(1H)-quinolinone (3.0 g), and para-toluenesulfonic acid (256 mg) was heated in refluxing toluene (50 ml), with azeotropic removal of water, for 40 hrs. An additional 2.0 g of the amine was added and the mixture was refluxed for 36 hrs. The solution was cooled and concentrated in vacuo. Sodium borohydride (0.6 g) was added to a solution of the residue in 50 ml of ethyl alcohol, and the mixture was stirred at room temperature for 1 hr. The mixture was concentrated in vacuo, the residue was quenched with water, and the mixture was extracted with dichloromethane. The combined organic layers were washed with brine, dried over anhydrous magnesium sulfate, filtered, and the filtrate was concentrated. Recrystallization of the residue from ethyl acetate/hexanes provided 2.5 g (42%) of product, mp 102°–103° C.

ANALYSIS: Calculated for $C_{18}H_{20}Cl_2N_2O$: 61.55% C, 5.74% H, 7.97% N. Found: 61.66% C, 5.86% H, 8.03% N.

EXAMPLE 29

5-[[2-(3,4-Dichlorophenyl)ethyl]amino]-5,6,7,8-tetrahydro-1-methyl-2(1H)-quinolinone A mixture of 2-(3,4-dichlorophenyl)ethylamine (3.8 g), 5,6,7,8-tetrahydro-1-methyl-5-oxo-2(1H)-quinolinone (3.0 g), and para-toluenesulfonic acid (130 mg) was heated in refluxing toluene (50 ml), with azeotropic removal of water, for 41 hrs. An additional 1 g of the amine and 0.1 g of para-toluenesulfonic acid were added, and the mixture was heated for an additional 24 hrs. The solution was cooled and the precipitate was collected. Sodium borohydride (0.6 g) was added to a solution of the precipitate in ethyl alcohol (50 ml), and the mixture was stirred at room temperature for 1 hr. The mixture was concentrated in vacuo, the residue was quenched with water, and the mixture was extracted with dichloromethane. The combined organic layers were washed with brine, dried over anhydrous magnesium sulfate, filtered, and the filtrate was concentrated. The residue was dissolved in hot ethanol and treated with an equivalent amount of fumaric acid. The solid was collected and recrystallized from ethanol to provide 3.8 g (48%) of product, mp 172°–173° C.

ANALYSIS: Calculated for $C_{22}H_{24}Cl_2N_2O_5$: 56.54% C, 5.18% H, 5.99% N. Found: 56.45% C, 5.04% H, 5.91% N.

EXAMPLE 30

5,6,7,8-Tetrahydro-1-methyl-5-[[2-(2,2-diphenyl)ethyl]amino]-2(1H)-quinolinone

A mixture of 2,2-diphenylethylamine (4.3 g), 5,6,7,8-tetrahydro-1-methyl-5-oxo-2(1H)-quinolinone (3.0 g), and para-toluenesulfonic acid (256 mg) was heated in 70 ml of refluxing toluene, with azeotropic removal of water, for 24 hrs. An additional 2.0 g of the amine was added, and the mixture was refluxed for 24 hrs. The solution was cooled and concentrated in vacuo. Sodium borohydride (0.6 g) was added to a solution of the residue in ethyl alcohol (70 ml), and the mixture was stirred at room temperature for 1 hr. The mixture was concentrated in vacuo, the residue was quenched with water, and the mixture brine, dried over anhydrous magnesium sulfate, filtered, and the filtrate was concentrated. Recrystallization of the residue from ethyl acetate/hexanes provided 3.4 g (57%) of product, mp 110°–112° C.

ANALYSIS: Calculated for $C_{24}H_{26}N_2O$: 80.41% C, 7.31% H, 7.81% N. Found: 80.42% C, 7.44% H, 7.63% N.

EXAMPLE 31

5,6,7,8-Tetrahydro-1-methyl-5-[(3-phenylpropyl)amino]-2(1H)-quinolinone fumarate A mixture of 3-phenylpropylamine (2.7 g), 5,6,7,8-tetrahydro-1-methyl-5-oxo-2(1H)-quinolinone (3.0 g), and para-toluenesulfonic acid (130 mg) was heated in refluxing toluene (50 ml), with azeotropic removal of water, for 24 hrs. An additional 1 g of the amine and 0.1 of para-toluenesulfonic acid were added, and the mixture was heated for an additional 18 hrs. The solution was cooled and concentrated in vacuo. Sodium borohydride (0.6 g) was added to a solution of the residue in ethyl alcohol (50 ml), and the mixture was stirred at room temperature for 1 hr. The mixture was concentrated in vacuo, the residue was quenched with water, and the mixture was extracted with dichloromethane. The combined organic layers were washed with brine, dried over anhydrous magnesium sulfate, filtered, and the filtrate was concentrated. The residue was washed with hexanes, dissolved in hot ethanol, and treated with an equivalent amount of fumaric acid to provide 5.5 g (80%) of product. Recrystallization from ethanol gave the analytical sample, mp 171°–173° C.

ANALYSIS: Calculated for $C_{23}H_{28}N_2O_5$: 66.97% C, 6.84% H, 6.79% N. Found: 66.77% C, 6.78% H, 6.78% N.

EXAMPLE 32

5-[[2-(4-Chlorophenyl)ethyl]amino]-5,6,7,8-tetrahydro-1,7,7-trimethyl-2-(1H)quinolinone fumarate A mixture of 5,6,7,8-tetrahydro-7,7-dimethyl-5-oxo-2(1H)-quinolinone (15.0 g), methyl iodide (12.3 g), potassium carbonate (21.6 g), and dimethylformamide (230 ml) was stirred at room temperature for 21 hrs. The reaction mixture was filtered, and the filtrate was concentrated. Ethyl acetate was added to the residue, and the mixture was filtered. The filtrate was washed with brine, dried over anhydrous magnesium sulfate, filtered, and the filtrate was concentrated to give 8.1 g (50%) of 5,6,7,8-tetrahydro-5-oxo-1,7,7-trimethyl-2(1H)-quinolinone.

A mixture of 5,6,7,8-tetrahydro-2-(4-chlorophenyl)ethylamine(3.6 g), 1,7,7-trimethyl-5-oxo-2(1H)-quinolinone (4.0 g), and para-toluenesulfonic acid (0.11 g) was heated in refluxing toluene (60 ml), with azeotropic removal of water, for 48 hrs, at which time an additional 3.6 g of amine and 0.1 g of para-toluenesulfonic acid were added. The mixture was refluxed for a total of 72 hrs. The mixture was cooled and concentrated in vacuo. Sodium borohydride (1.0 g) was added to a solution of the residue in ethyl alcohol (50 ml), and the mixture was stirred at room temperature for 1 hr. The mixture was concentrated in vacuo, the residue was quenched with water, and the mixture was extracted with dichloromethane. The combined organic layers were washed with brine, dried over anhydrous magnesium sulfate, filtered, and the filtrate was concentrated. The residue was purified by high performance liquid chromatography (silica gel, eluted with methanol/ethyl acetate). The appropriate fractions were collected and evaporated. The residue was dissolved in methanol and treated with 0.74 g of fumaric acid. The mixture was evaporated, and the residue triturated with ethyl acetate to give 2.8 g (31%) of product. Recrystallization from ethanol give the analytical sample, mp 155°–156° C.

ANALYSIS: Calculated for $C_{24}H_{29}ClN_2O_5$: 62.54% C, 6.34% H, 6.08% N. Found: 62.32% C., 6.21% H, 6.43% N.

EXAMPLE 33

5-[[2-(3,4,-Dichlorophenyl)ethyl]amino]-5,6,7,8-tetrahydro-1-propyl-2(1H)-quinolinone A mixture of 2-(3,4-dichlorphenyl)ethylamine (4.2 g) 5,6,7,8-tetrahydro-1-propyl-5-oxo-2(1H)-quinolinone (3.5 g), and para-toluenesulfonic acid (257 mg) was heated in refluxing toluene (70 ml), with azeotropic removal of water, for 40 hrs. An additional 1 g of the amine was added after 40 and 64 hrs. The mixture was heated for a total of 88 hrs. The solution was cooled and evaporated in vacuo.

Sodium borohydride (0.60 g) was added to a solution of the residue in ethyl alcohol (70 ml), and the mixture was stirred at room temperature for 1 hr. The mixture was evaporated in vacuo. The residue was quenched with water, and the mixture was extracted with dichloromethane. The combined organic layers were washed with brine, dried over anhydrous magnesium sulfate, filtered, and the filtrate was concentrated. The residue was purified by high performance liquid chromatography on silica gel (elution with methanol/ethyl acetate to afford 4.8 g (75%) of product. Recrystallization from ethyl acetate/hexanes provided the analytical sample, mp 105°–107° C.

ANALYSIS: Calculated for $C_{20}H_{24}Cl_2N_2O$: 63.33% C., 6.38% C., 7.38% N. Found: 63.10% C., 6.22% H, 7.36% N.

EXAMPLE 34

5,6,7,8-Tetrahydro-1-methyl-5-[[2-(1-napthyl)ethyl]amino]-2(1H)-quinolinone fumarate A mixture of 2-(1-naphthyl)ethylamine(3.7 g), 5,6,7,8-tetrahydro-1-methyl-5-oxo-2(1H)-quinolinone (3.0 g), and para-toluenesulfonic acid (256 mg) was heated in refluxing toluene (70 ml), with azeotropic removal of water, for 24 hrs. An additional 2 g of the amine was added, and the mixture was heated for an additional 24 hrs. The solution was cooled and evaporated in vacuo.

Sodium borohydride (0.60 g) was added to a solution of the residue in ethyl alcohol (70 ml), and the mixture was stirred at room temperature for 1 hr. The mixture was evaporated in vacuo, the residue was quenched with water, and the mixture was extracted with dichloromethane. The combined organic layers were washed with brine, dried over anhydrous magnesium sulfate, filtered, and the filtrate concentrated. The residue was purified by high performance liquid chromatography on silica gel (elution with methanol/ethyl acetate) to afford 4.59 g (82%) of product. The product was dissolved in methanol and treated with an equivalent amount of fumaric acid. The solution was evaporated in vacuo, and the residue was recrystallized from methanol. The solid was stirred in hot methanol, and the mixture was filtered to provide the analytical sample, mp 189°–191° C.

ANALYSIS: Calculated for $C_{26}H_{28}N_2O_5$: 69.33% C., 6.29% H, 6.25% N. Found: 69.38% C., 6.39% H, 6.21% N.

EXAMPLE 35

5-[[2-(4-Chlorophenyl)ethyl]amino]-5,6,7,8-tetrahydro-1-(2-propenyl)-2(1H)-quinolinone hydrochloride A mixture of 2-(4-chlorophenyl)ethylamine (5.5 g), 5,6,7,8-tetrahydro-5-oxo-(2-propenyl)-2(1H)-quinolinone (6.0 g), and para-toluenesulfonic acid (450 mg) was heated in refluxing toluene (100 ml), with azeotropic removal of water, for 24 hrs. An additional 2 g of the amine was added, and the mixture was heated for an additional 48 hrs. The solution was cooled and evaporated in vacuo.

Sodium borohydride (1.12 g) was added to a solution of the residue in ethyl alcohol (100 ml), and the resulting mixture was stirred at room temperature for 1 hr. The mixture was evaporated in vacuo, the residue was quenched with water, and the mixture was extracted with dichloromethane. The combined organic layers were washed with brine, dried over anhydrous magnesium sulfate, filtered, and the filtrate was concentrated. The residue was purified by high performance liquid chromatography on silica gel (elution with 5% methanol/ethyl acetate to provide 8.50 g (85%) of product. A portion of product was dissolved in methanol and treated with ethereal hydrogen chloride. The mixture was evaporated in vacuo, and the residue was crystallized from methanol/isopropyl ether to provide the analytical sample, mp 175°–177° C.

ANALYSIS: Calculated for $C_{20}H_{24}Cl_2N_2O$: 63.33% C., 6.38% H, 7.38% N. Found: 63.00% C., 6.53% H, 7.03% N.

EXAMPLE 36

5-[[2-(4-Chlorophenyl)ethyl]amino]-5,6,7,8-tetrahydro-1-propyl-2(1H)-quinolinone fumarate A mixture of 5-[[2-(4-chlorophenyl)ethyl]amino]-5,6,7,8-tetrahydro-1-(2-propenyl)-2(1H)-quinolinone (4.5 g) and 10% palladium-on-carbon (0.45 mg) in ethanol (100 ml) was stirred under an atmosphere of hydrogen for 3 hrs. The mixture was filtered through celite, and the filtrate was concentrated. The residue was filtered through silica gel (elution with ethyl acetate/methanol), and the filtrate was evaporated. The residue was dissolved in ethanol, treated with an equivalent amount of fumaric acid, and the salt was allowed to crystallize. The precipitate was collected to provide 3.0 g (50%) of product, mp 166°–168° C.

ANALYSIS: Calculated for $C_{24}H_{29}ClN_2O_5$: 62.54% C, 6.34% H, 6.08% N. Found: 62.73% C, 6.19% H, 6.05% N.

EXAMPLE 37

5-[[2-(3,4-Dichlorophenyl)ethyl]amino]-1-hexyl-5,6,7,8-tetrahydro-2(1H)-quinolinone fumarate A mixture of 5,6,7,8-tetrahydro-5-oxo-2(1H)-quinolinone (10.0 g), lithium hydride (0.78 g), and dimethylformamide (400 ml) was stirred for 3 hrs at 25° C., under nitrogen. 1-Bromohexane (10.6 g) was added and the mixture was stirred for an additional eighteen hrs. The reaction mixture was concentrated and the residue was partitioned between ethyl acetate and water. The layers were separated and the aqueous layer was extracted with ethyl acetate. The combined organic extracts were washed with water and brine, dried over anhydrous magnesium sulfate, filtered, and the filtrate was concentrated. The residue was purified by high performance liquid chromatography (silica gel, two columns, eluted with 50% ethyl acetate/hexane). The appropriate fractions were collected and evaporated to give 4.6 (31%) of 1-hexyl-5,6,7,8-tetrahydro-5-oxo-2(1H)-quinolinone.

Titanium tetra-isopropoxide (11.6 g) was rapidly added dropwise to a suspension of 1-hexyl-5,6,7,8-tetrahydro-5-oxo-2(1H)-quinolinone (4.6 g) and 3,4-dichlorophenethylamine (7.0 g) in acetonitrile (38 ml). The mixture was stirred at room temperature for 20 hrs and water and dichloromethane were added. The layers were separated, and the aqueous phase was extracted with dichloromethane. The combined organic phases were filtered, dried over anhydrous magnesium sulfate, filtered, and the filtrate was concentrated.

Sodium borohydride (706 mg) was added to a solution of the residue in ethyl alcohol (80 ml), and the mixture was stirred at room temperature for 1 hr. The mixture was evaporated in vacuo, the residue was quenched with water, and the mixture was extracted with dichloromethane. The combined organic layers were washed with brine, dried over anhydrous magnesium sulfate, filtered, and the filtrate was concentrated. The residue was purified by high performance liquid chromatography on silica gel (elution with 5% methanol/ethyl acetate) to provide 5.8 g (74%) of product. The product was dissolved in ethanol and treated with an equivalent amount of fumaric acid. The mixture was concentrated in vacuo, ethyl acetate was added, and the product was allowed to crystallize to provide the analytical sample, mp 160°–162° C.

ANALYSIS: Calculated for $C_{27}H_{34}Cl_2N_2O_5$: 60.34% C, 6.38% H, 5.21% N Found: 60.01% C, 6.26% H, 5.05% N.

EXAMPLE 38

5-[[2-(3,4-Dichlorophenyl)ethyl]amino]-5,6,7,8-tetrahydro-1-(3-methyl-2-butenyl)-2(1H)-quinolinone maleate A mixture of 5,6,7,8-tetrahydro-5-oxo-(2(1H)-quinolinone (10.0 g), lithium hydride (0.79), and dimethylformamide (400 ml) was stirred for 3 hrs at 25° C., under nitrogen. 3-Methylbutenyl bromide (10.6) was added and the mixture was stirred for an additional eighteen hrs. The reaction mixture was concentrated and the residue was partitioned between ethyl acetate and water. The layers were separated and the aqueous layer was extracted with ethyl acetate. The combined organic extracts were washed with water and brine, dried over anhydrous magnesium sulfate, filtered, and the filtrate was concentrated. The residue was triturated with petroleum ether to afford 10.5 g (74 %) of 5,6,7,8-tetrahydro-1-(3-methyl-2-buteneyl)-5-oxo-2(1H)-quinolinone.

A mixture of 3,4-dichlorophenethylamine (7.9 g), 5,6,7,8-tetrahydro-1-(3-methyl-2-butenyl)-5-oxo-2(1H)-quinolinone (8.0 g), and para-toluenesulfonic acid (526 mg) was heated in refluxing toluene (100 ml), with azeotropic removal of water, for 18 hrs. An additional 2 g of the amine was added, and the mixture was heated for an additional 68 hrs. The solution was cooled and evaporated in vacuo.

Sodium borohydride (1.3 g) was added to a solution of the residue in ethyl alcohol (100 ml), and the mixture was stirred at room temperature for 1 hr. The mixture was evaporated in vacuo, the residue was quenched with water, and the mixture was extracted with dichloromethane. The combined organic layers were washed with brine, dried over anhydrous magnesium sulfate, filtered, and the filtrate was concentrated. The residue was purified by high performance liquid chromatography on silica gel (elution with methanol/ethyl acetate) to afford 11.5 g (82%) of product as an oil. The product was dissolved in hot ethanol and treated with an equivalent amount of maleic acid. The solution was allowed to cool, the precipitate was collected to provide the analytical sample, mp 103°–107° C.

ANALYSIS: Calculated for $C_{26}H_{30}Cl_2N_2O_5$: 59.89% C, 5.80% H, 5.37% N. Found: 59.35% C, 5.51% H, 5.32% N.

EXAMPLE 39

5,6,7,8-Tetrahydro-1-methyl-5-[[2-(2-napthyl)ethyl]amino]-2(1H)-quinolinone

Titanium tetra-isopropoxide (10.5 g) was rapidly added to a solution of 5,6,7,8-tetrahydro-1-methyl-5-oxo-2(1H)-quinolinone (3.0 g) and 2-(2-napthyl)ethylamine (5.8 g) in acetonitrile (35 ml). The mixture was stirred at room temperature for 20 hrs and dichloromethane and water were added. The mixture was filtered, the layers of the filtrate were separated, and the aqueous phase was extracted with dichloromethane. The combined organic phases were dried over anhydrous magnesium sulfate, filtered, and the filtrate was concentrated.

Sodium borohydride (600 mg) was added to a solution of the residue in ethyl alcohol (100 ml), and the mixture was stirred at room temperature for 1 hr. The mixture was concentrated in vacuo, the residue was quenched with water, and the mixture was extracted with dichloromethane. The combined organic layers were washed with brine, dried over anhydrous magnesium sulfate, filtered, and the filtrate was concentrated. The residue was recrystallized twice from ethyl acetate to provide 2.5 g (45%) of product, mp 113°–115° C.

ANALYSIS: Calculated for $C_{22}H_{24}N_2O$: 79.48% C, 7.28% H, 8.43% N. Found: 79.66% C, 7.43% H, 8.48% N.

EXAMPLE 40

5-[[2-(3,4-Dichlorophenyl)ethyl]amino]-5,6,7,8-tetrahydro-1-(2-phenylethyl)-2(1H)-quinolinone A mixture of 5,6,7,8-tetrahydro-5-oxo-2(1H)-quinolinone (7.5 g), lithium hydride (0.59 g), and dimethylformamide (300 ml) was stirred for 3 hrs at 25° C., under nitrogen. 2-Phenylethyl bromide (9.36 g) was added and the mixture was stirred for an additional eighteen hrs. The reaction mixture was concentrated and the residue was partitioned between ethyl acetate and water. The layers were separated and the aqueous layer was extracted with ethyl acetate. The combined organic extracts were washed with water and brine, dried over anhydrous magnesium sulfate, filtered, and the filtrate was concentrated. The residue was triturated with petroleum ether to afford 3.0 g (24%) of 5,6,7,8-tetrahydro-5-oxo-1-(2-phenylethyl)-2(1H)-quinolinone.

Titanium tetra-isopropoxide (7.0 g) was rapidly added to a solution of 5,6,7,8-tetrahydro-5-oxo-1-(2-phenylethyl)-2(1H)-quinolinone (3.0 g), and 2-(3,4-dichlorophenyl)ethylamine (5.8 g) in acetonitrile (25 ml). The mixture was stirred at room temperature for 20 hrs and dichloromethane and water were added. The mixture was filtered, the layers of the filtrate were separated, and the aqueous phase was extracted with dichloromethane. The combined organic phases were dried over anhydrous magnesium sulfate, filtered, and the filtrate was concentrated.

Sodium borohydride (420 mg) was added to a solution of the residue in ethyl alcohol (50 ml), and the mixture was stirred at room temperature for 1 hr. The mixture was concentrated in vacuo, the residue was quenched with water, and the mixture was extracted with dichloromethane. The combined organic layers were washed with brine, dried over anhydrous magnesium sulfate, filtered, and the filtrate was concentrated. Recrystallization of the residue from ethyl acetate/hexanes provided 2.6 g (52%) of product, mp 120°–122° C.

ANALYSIS: Calculated for $C_{25}H_{26}Cl_2N_2O$: 68.03% C, 5.94% H, 6.35% N. Found: 68.01% C, 5.81% H, 6.27% N.

EXAMPLE 41

5-[[2-(1-Cyclohexenyl)ethyl]amino]-5,6,7,8-tetrahydro-1-methyl-2(1H)-quinolinone Titanium tetra-isopropoxide (21.0 g) was rapidly added to a solution of 5,6,7,8-tetrahydro-5-oxo-1-methyl)-2(1H)-quinolinone (6.0 g) and 2-(1-cyclohexenyl)ethylamine (8.4 g) in acetonitrile (70 ml). The mixture was stirred at room temperature for 20 hrs and dichloromethane and water were added. The mixture was filtered, the layers of the filtrate were separated, and the aqueous phase was extracted with dichloromethane. The combined organic phases were dried over anhydrous magnesium sulfate, filtered, and the filtrate was concentrated.

Sodium borohydride (1.2 mg) was added to a solution of the residue in ethyl alcohol (150 ml), and the mixture was stirred at room temperature for 1 hr. The mixture was concentrated in vacuo, the residue was carefully quenched with water, and the mixture was extracted with dichloromethane. The combined organic layers were washed with brine, dried over anhydrous magnesium sulfate, filtered, and the filtrate concentrated. Recrystallization or the residue from ethyl acetate/hexanes provided 3.5 g (32%) of product, mp 184°–187° C.

ANALYSIS: Calculated for $C_{18}H_{26}N_2O$: 75.48% C, 9.15% H, 9.78% N. Found: 75.69% C, 9.32% H, 9.79% N.

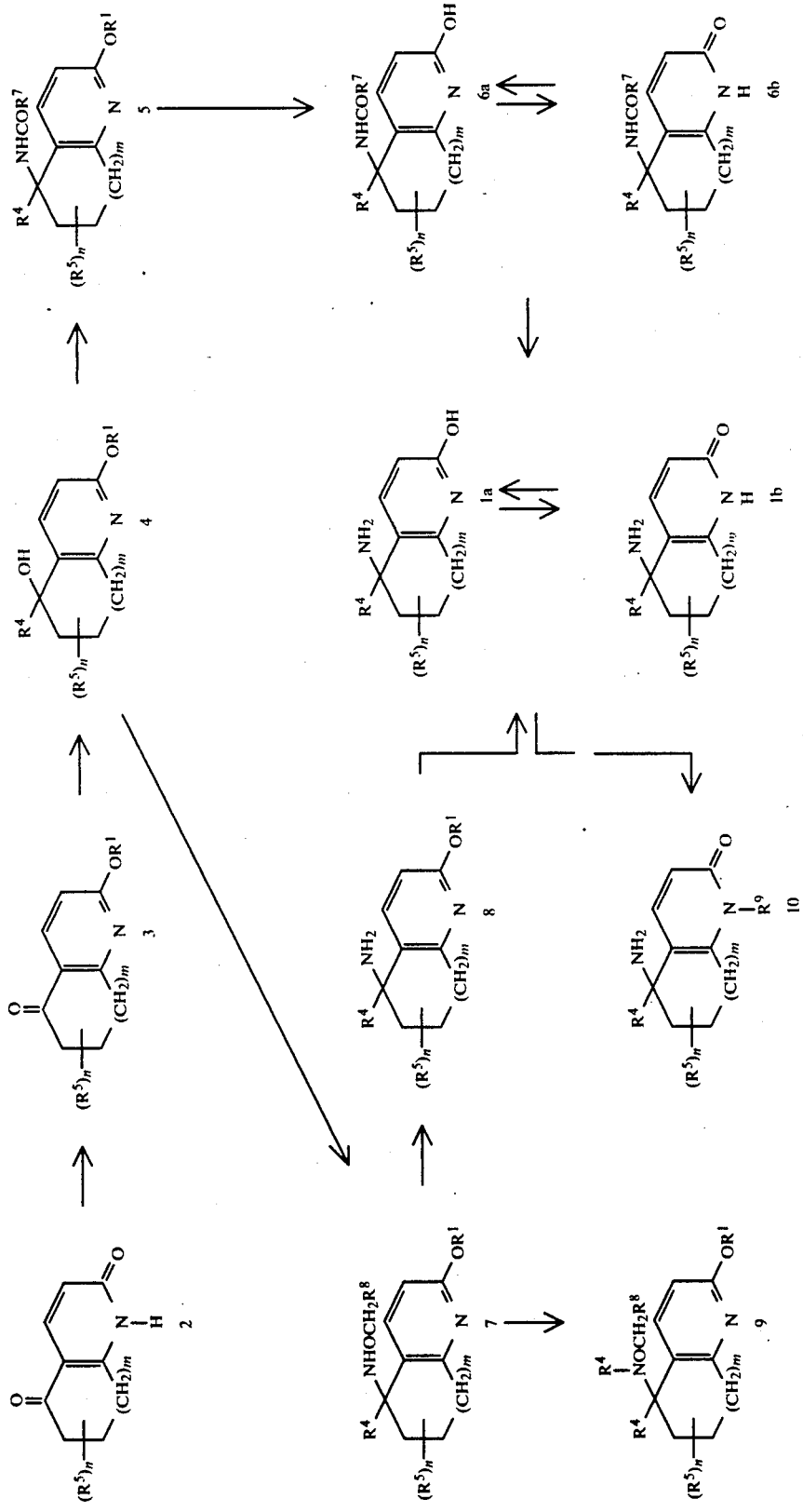
REACTION SCHEME A
wherein $R^1$, $R^4$, $R^5$, $R^7$, $R^8$, $R^9$, m, and n are as hereinbefore described REACTION SCHEME B
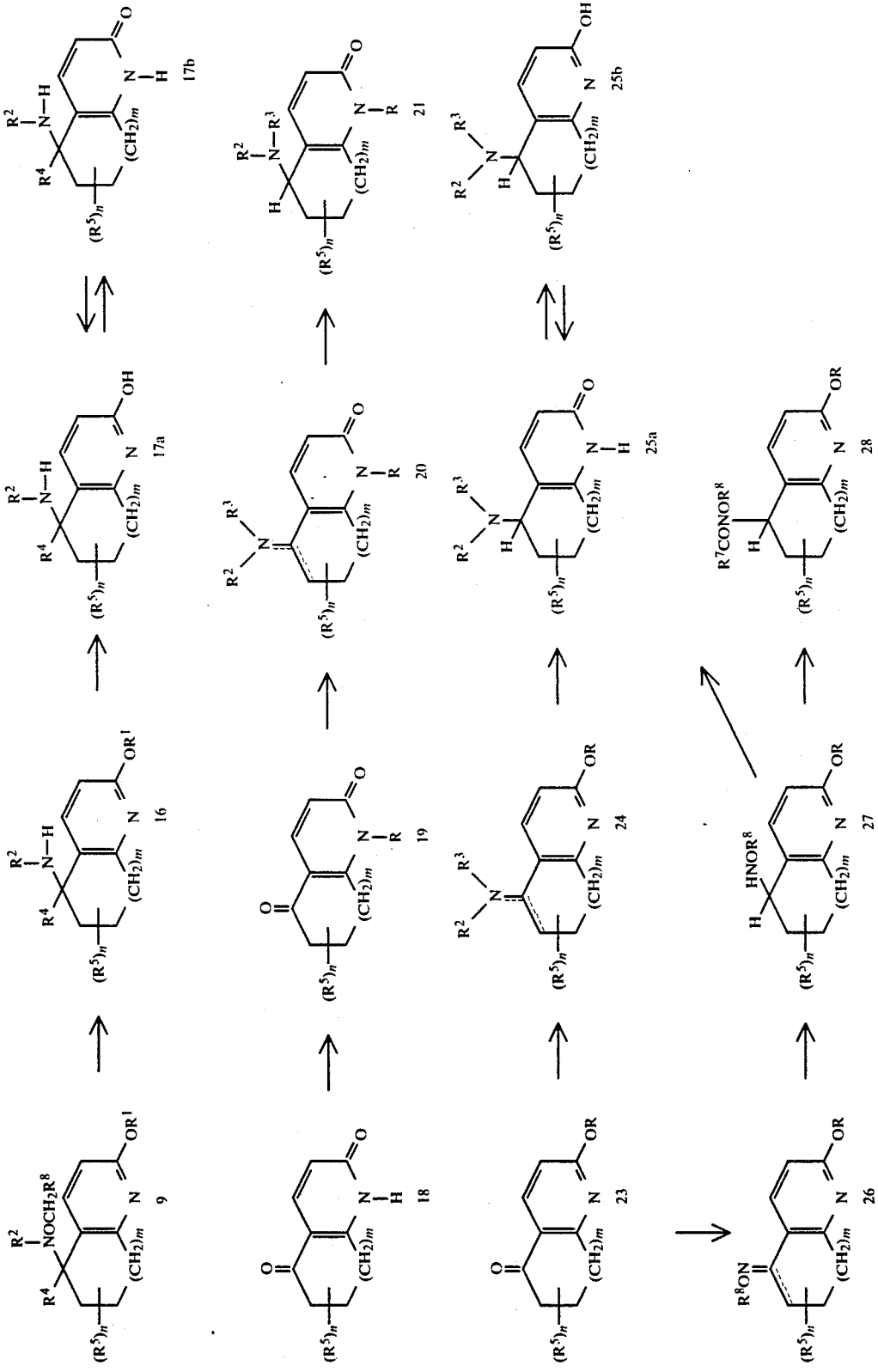
wherein R, R¹, R², R³, R⁴, R⁵, R⁶, R⁷, R⁸, m, and n are as hereinbefore described

We claim:
1. A compound of the formula

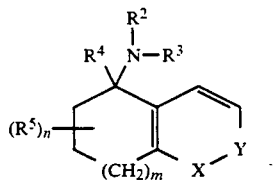

wherein X-Y is a group of the formula

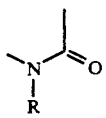

wherein R is hydrogen, loweralkyl, loweralkenyl, loweralkynl, or arylloweralkyl, or a group of the formula

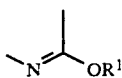

wherein $R^1$ is hydrogen, loweralkyl or arylloweralkyl; $R^2$ and $R^3$ are independently hydrogen, loweralkyl, arylloweralkyl, diarylloweralkyl, lowercycloalkenyl-loweralkyl, loweralkoxy, arylloweralkoxy, or loweralkanoyl; $R^2$ and $R^3$ taken together with the nitrogen atom to which they are attached form a group of the formula

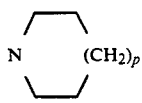

wherein p is 0 or 1, a group of the formula

wherein Z is O, S, or a group of the formula $NR^6$ wherein $R^6$ is hydrogen, loweralkyl, or arylloweralkyl; $R^4$ is hydrogen, loweralkyl, or arylloweralkyl; $R^5$ is hydrogen, loweralkyl, or arylloweralkyl; m is 0, 1, or 2; and n is 1 or 2; with the proviso that when $R^2$ and $R^3$ are hydrogen, or either $R^2$ or $R^3$ is loweralkyl, and X-Y is a group of the formula

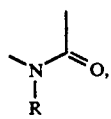

$R^4$ is not hydrogen or loweralkyl; the geometric and optical isomers thereof, or a pharmaceutically acceptable salt thereof.

2. A compound according to claim 1 wherein X-Y is a group of the formula

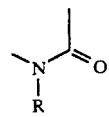

and m is 1.

3. A compound according to claim 1 wherein X-Y is a group of the formula

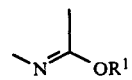

wherein m is 1.

4. The compound according to claim 2 which is 5-amino-5,6,7,8-tetrahydro-5-(phenylmethyl)-2(1H)-quinolinone.

5. The compound according to claim 2 which is N-(1,2,5,6,7,8-hexahydro-5-methyl-2-oxo-5-quinolinyl)acetamide.

6. The compound according to claim 2 which is 5,6,7,8-tetrahydro-5-[(2-phenylethyl)amino]-2-(1H)-quinolinone.

7. The compound according to claim 2 which is 5,6,7,8-tetrahydro-1-methyl-5-[(2-phenylethyl)amino]-2(1H)-quinolinone.

8. The compound according to claim 3 which is 5,6,7,8-tetrahydro-5-methyl-2-(phenylmethoxy)-5-quinolinamine.

9. The compound according to claim 3 which is 5,6,7,8-tetrahydro-N,5-dimethyl-N,2-bis(phenylmethoxy)-5-quinolinamine.

10. The compound according to claim 3 which is 5,6,7,8-tetrahydro-N,5-dimethyl-2-(phenylmethoxy)-5-quinolinamine.

11. The compound according to claim 3 which is 5,6,7,8-tetrahydro-2-(phenylmethoxy)-5-(phenylmethyl)-5-quinolinamine.

12. The compound according to claim 3 which is 5,6,7,8-tetrahydro-N,2-bis(phenylmethoxy)-5-(phenylmethyl)-5-quinolinamine.

13. The compound according to claim 3 which is 5,6,7,8-tetrahydro-N-[5-methyl-2-(phenylmethoxy)-5-quinolinyl]acetamide.

14. The compound according to claim 3 which is 5,6,7,8-tetrahydro-N,2-bis(phenylmethoxy)-5-quinolinamine.

15. The compound according to claim 3 which is 5,6,7,8-tetrahydro-N-(phenylmethoxy)-2-(phenylmethoxy)-5-quinolinylacetamide.

16. The compound according to claim 3 which is 5,6,7,8-tetrahydro-5-(2-phenethylamino)-2-phenylmethoxy)quinoline.

17. The compound according to claim 3 which is 5,6,7,8-tetrahydro-5-methyl-N,2-bis(phenylmethoxy)-5-quinolinamine.

18. A method of relieving memory dysfunction in mammals comprising administering to a mammal requiring memory dysfunction relief, a memory dysfunction relieving effective amount of a compound of claim 1.

19. A memory dysfunction relieving composition comprising an adjuvant and as the active ingredient, a memory dysfunction relieving effectiv amount of a compound of claim 1.

20. A compound of the formula

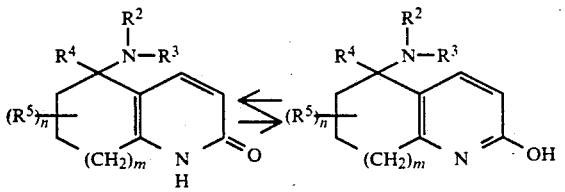

wherein $R^2$ and $R^3$ are independently hydrogen, loweralkyl, arylloweralkyl, lowercycloalkenylloweralkyl, loweralkoxy, arylloweralkoxy, or loweralkanoyl, and $R^2$ and $R^3$ taken together with the nitrogen atom to which they are attached form a group of the formula

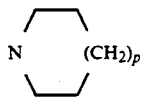

wherein p is 0 or 1, a group of the formula

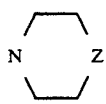

wherein Z is O, S, or a group of the formula $NR^6$ wherein $R^6$ is hydrogen, loweralkyl, or arylloweralkyl; $R^4$ is hydrogen, loweralkyl or arylloweralkyl; $R^5$ is hydrogen, loweralkyl or arylloweralkyl; m is 0, 1, or 2; and n is 1 or 2; with the proviso that when $R^2$ and $R^3$ are hydrogen, or either $R^2$ or $R^3$ is loweralky, and X-Y is a group of the formula

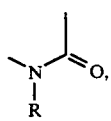

$R^4$ is not hydrogen or loweralkyl; the geometric and optical isomers thereof, or a pharmaceutically acceptable salt thereof.

21. A compound according to claim 20 of the formula

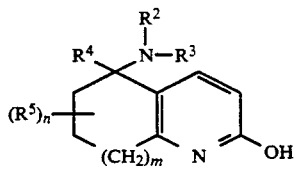

22. A compound according to claim 20 of the formula

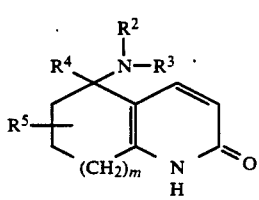

23. The compound according to claim 2 which is 5,6,7,8-tetrahydro-5-[(2-phenylethyl)amino]-1-(2-propenyl)-2(1H)-quinolinone.

24. The compound according to claim 2 which is 5-[[2-(3,4-dichlorophenyl)ethyl]amino-5,6,7,8-tetrahydro-1-(2-propenyl)-2(1H)-quinolinone.

25. The compound according to claim 2 which is 5,6,7,8-tetrahydro-5-[(2-phenylethyl)amino]-1-propyl-2(1H)-quinolinone.

26. The compound according to claim 2 which is 5-[[2-(3,4-dichlorophenyl)ethyl]amino-5,6,7,8-tetrahydro-1-(phenylmethyl)-2(1H)quinolinone.

27. The compound according to claim 2 which is 5,6,7,8-tetrahydro-1-methyl-5-[(phenylmethyl)amino]-2(1H)-quinolinone.

28. The compound according to claim 2 which is 5-[[2-(4-trifluoromethylphenyl)ethyl]amino]-5,6,7,8-tetrahydro-1-methyl-2(1H)-quinolinone.

29. The compound according to claim 2 which is 5,6,7,8-tetrahydro-5-[[2-(4-nitrophenyl)ethyl]amino]-1-methyl-2(1H)-quinolinone.

30. The compound according to claim 2 which is 5-[[2-(4-chlorophenyl)-ethyl]amino]-5,6,7,8-tetrahydro-1-methyl-2(1H)-quinolinone.

31. The compound according to claim 2 which is 5,6,7,8-tetrahydro-5-[[2-(4-methoxyphenyl)ethyl]amino]-1-methyl-2(1H)-quinolinone.

32. The compound according to claim 2 which is 5,6,7,8-tetrahydro-1-methyl-5-[[2-(4-methylphenyl)-ethyl]amino]-2(1H)-quinolinone.

33. The compound according to claim 2 which is 5-[[2-(2,4-dichlorophenyl)ethyl]amino]-5,6,7,8-tetrahydro-1-methyl-2-(1H)-quinolinone.

34. The compound according to claim 2 which is 5-[[2-(3,4-dichlorophenyl)ethyl]amino]-5,6,7,8-tetrahydro-1-methyl-2(1H)-quinolinone.

35. The compound according to claim 2 which is 5,6,7,8-tetrahydro-1-methyl-5-[[2-(2,2-diphenyl)-ethyl]amino]-2(1H)-quinolinone.

36. The compound according to claim 2 which is 5,6,7,8-tetrahydro-1-methyl-5-[(3-phenylpropyl)amino]-2(1H)-quinolinone.

37. The compound according to claim 2 which is 5-[[2-(4-chlorophenyl)ethyl]amino]-5,6,7,8-tetrahydro-1,7,7-trimethyl-2(1H)-quinolinone.

38. The compound of claim 2 which 5-[[2-(3,4-dichlorophenyl)-ethyl]amino]-5,6,7,8-tetrahydro-1-propyl-2(1H)-quinolinone.

39. The compound of claim 2 which is 5,6,7,8-tetrahydro-1-methyl-5-[[2-(1-napthyl)ethyl]amino]-2(1H)-quinolinone.

40. The compound of claim 2 which is 5-[[2-(4-chlorophenyl)-ethyl]amino]-5,6,7,8-tetrahydro-1-(2-propenyl)-2(1H)-quinolinone.

41. The compound of claim 2 which is 5-[[2-(4-chlorophenyl)-ethyl]amino]-5,6,7,8-tetrahydro-1-propyl-2(1H)-quinolinone.

42. The compound of claim 2 which is 5-[[2-(3,4-dichlorophenyl)-ethyl]amino-1-hexyl-5,6,7,8-tetrahydro-2(1H)-quinolinone.

43. The compound of claim 2 which is 5-[[2-(3,4-dichlorophenyl)-ethyl]amino]-5,6,7,8-tetrahydro-1-(3-methyl-2-butenyl)-2(1H)-quinolinone.

44. The compound of claim 2 which is 5,6,7,8-tetrahydro-1-methyl-5-[[2-(2-naphthyl)ethyl]amino]-2(1H)-quinolinone.

45. The compound of claim 2 which is 5-[[2-(3,4-dichlorophenyl)-ethyl]amino]-5,6,7,8-tetrahydro-1-(2-phenylethyl)-2(1H)-quinolinone.

46. The compound of claim 2 which is 5-[[2-(1-cyclohexenyl)-ethyl]amino]-5,6,7,8-tetrahydro-1-methyl-2(1H)-quinolinone.

* * * * *